(12) United States Patent
Morton et al.

(10) Patent No.: US 9,562,866 B2
(45) Date of Patent: Feb. 7, 2017

(54) COVERT SURVEILLANCE USING MULTI-MODALITY SENSING

(71) Applicant: Rapiscan Systems, Inc., Torrance, CA (US)

(72) Inventors: Edward James Morton, Guildford (GB); Joseph Bendahan, San Jose, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 128 days.

(21) Appl. No.: 14/531,437

(22) Filed: Nov. 3, 2014

(65) Prior Publication Data

US 2015/0330917 A1   Nov. 19, 2015

Related U.S. Application Data

(63) Continuation of application No. 13/523,604, filed on Jun. 14, 2012, now Pat. No. 8,908,831, which is a
(Continued)

(51) Int. Cl.
  *G01N 23/00*  (2006.01)
  *G01N 23/203* (2006.01)
  (Continued)

(52) U.S. Cl.
  CPC .......... *G01N 23/203* (2013.01); *G01N 23/005* (2013.01); *G01V 5/0041* (2013.01); *G21K 1/043* (2013.01)

(58) Field of Classification Search
  CPC G01N 23/005; G01N 23/203; G01N 23/0041; G21K 1/043; G01B 5/0041
  See application file for complete search history.

(56) References Cited

U.S. PATENT DOCUMENTS 4,745,631 A * 5/1988 Paolini ............... G21K 5/10
                                                   250/224
5,038,370 A   8/1991 Harding
(Continued)

FOREIGN PATENT DOCUMENTS

WO   2011008718       1/2011
WO   2011069024 A1    6/2011
(Continued)

OTHER PUBLICATIONS

Office Action for Canadian Patent Application No. 2,863,363, dated Nov. 3, 2015.
(Continued)

*Primary Examiner* — David J Makiya
*Assistant Examiner* — Dani Fox
(74) *Attorney, Agent, or Firm* — Novel IP; Hazim Ansari; Sona Dalal

(57) ABSTRACT

The present specification discloses a covert mobile inspection vehicle with a backscatter X-ray scanning system that has an X-ray source and detectors for obtaining a radiographic image of an object outside the vehicle. The system is configured to also simultaneously detect passive radiation. The systems preferably include at least one sensor for determining a distance from at least one of the detectors to points on the surface of the object being scanned, a processor for processing the obtained radiographic image by using the determined distance of the object to obtain an atomic number of each material contained in the object, and one or more sensors to obtain surveillance data from a predefined area surrounding the vehicle.

20 Claims, 20 Drawing Sheets

Related U.S. Application Data continuation-in-part of application No. 13/368,202, filed on Feb. 7, 2012, now Pat. No. 8,903,046.

(60) Provisional application No. 61/497,024, filed on Jun. 14, 2011, provisional application No. 61/440,834, filed on Feb. 8, 2011.

(51) Int. Cl.
    *G01V 5/00*      (2006.01)
    *G21K 1/04*      (2006.01)

(56) References Cited

U.S. PATENT DOCUMENTS

| | | |
|---|---|---|
| 5,179,581 A | 1/1993 | Annis |
| 5,185,778 A | 2/1993 | Magram |
| 5,224,144 A | 6/1993 | Annis |
| 5,253,283 A | 10/1993 | Annis |
| 5,313,511 A | 5/1994 | Annis |
| 5,493,596 A | 2/1996 | Annis |
| 5,666,393 A | 9/1997 | Annis |
| 5,696,806 A | 12/1997 | Grodzins |
| 5,744,919 A | 4/1998 | Mishin |
| 5,757,472 A | 5/1998 | Wangler |
| 5,764,683 A | 6/1998 | Swift |
| 5,903,623 A | 5/1999 | Swift |
| 5,910,973 A | 6/1999 | Grodzins |
| 5,930,326 A | 7/1999 | Rothschild |
| 5,940,468 A | 8/1999 | Huang |
| 6,067,344 A | 5/2000 | Grodzins |
| 6,081,580 A | 6/2000 | Grodzins |
| 6,151,381 A | 11/2000 | Grodzins |
| 6,192,104 B1 | 2/2001 | Adams |
| 6,249,567 B1 | 6/2001 | Rothschild |
| 6,282,260 B1 | 8/2001 | Grodzins |
| 6,292,533 B1 | 9/2001 | Swift |
| 6,320,933 B1 | 11/2001 | Grodzins |
| 6,356,620 B1 | 3/2002 | Rothschild |
| 6,421,420 B1 | 7/2002 | Grodzins |
| 6,424,695 B1 | 7/2002 | Grodzins |
| 6,434,219 B1 | 8/2002 | Rothschild |
| 6,442,233 B1 | 8/2002 | Grodzins |
| 6,453,007 B2 | 9/2002 | Adams |
| 6,459,761 B1 | 10/2002 | Grodzins |
| 6,459,764 B1 | 10/2002 | Chalmers |
| 6,542,574 B2 | 4/2003 | Grodzins |
| 6,546,072 B1 | 4/2003 | Chalmers |
| 6,621,888 B2 | 9/2003 | Grodzins |
| 6,658,087 B2 | 12/2003 | Chalmers |
| 6,744,845 B2 | 6/2004 | Harding |
| 7,010,094 B2 | 3/2006 | Grodzins |
| 7,099,434 B2 | 8/2006 | Adams |
| RE39,396 E | 11/2006 | Swift |
| 7,218,704 B1 | 5/2007 | Adams |
| 7,250,940 B2 | 7/2007 | Jayanetti |
| 7,400,701 B1 | 7/2008 | Cason |
| 7,505,556 B2 | 3/2009 | Chalmers |
| 7,505,562 B2 | 3/2009 | Dinca |
| 7,538,325 B2 | 5/2009 | Mishin |
| 7,551,714 B2 | 6/2009 | Rothschild |
| 7,551,715 B2 | 6/2009 | Rothschild |
| 7,551,718 B2 | 6/2009 | Rothschild |
| 7,555,099 B2 | 6/2009 | Rothschild |
| 7,593,506 B2 | 9/2009 | Cason |
| 7,593,510 B2 | 9/2009 | Rothschild |
| 7,796,734 B2 | 9/2010 | Mastronardi |
| 7,809,109 B2 | 10/2010 | Mastronardi |
| 7,957,506 B2 | 6/2011 | Smith |
| 8,194,822 B2 | 6/2012 | Rothschild |
| 8,275,091 B2 | 9/2012 | Morton |
| 8,325,871 B2 † | 12/2012 | Grodzins |
| 8,389,941 B2 | 3/2013 | Bendahan |
| 8,451,974 B2 | 5/2013 | Morton |
| 8,483,356 B2 | 7/2013 | Bendahan |
| 8,503,605 B2 | 8/2013 | Morton |
| 8,582,720 B2 | 11/2013 | Morton |
| 2005/0088644 A1 | 4/2005 | Morcom |
| 2009/0175412 A1* | 7/2009 | Grodzins ............... G01N 23/04 378/57 |
| 2009/0257555 A1 | 10/2009 | Chalmers |
| 2011/0038453 A1 | 2/2011 | Morton |
| 2011/0064192 A1 | 3/2011 | Morton |
| 2011/0075808 A1 | 3/2011 | Rothschild |
| 2011/0135060 A1 | 6/2011 | Morton |
| 2012/0236990 A1 | 9/2012 | Rothschild |
| 2013/0039472 A1 | 2/2013 | Morton |
| 2013/0343520 A1 | 12/2013 | Grodzin |

FOREIGN PATENT DOCUMENTS

| | | |
|---|---|---|
| WO | 2011095810 | 8/2011 |
| WO | 2012109273 | 8/2012 |
| WO | 2012174265 | 12/2012 |

OTHER PUBLICATIONS

European Search Report for EP12801343.0, Jun. 10, 2015.
International preliminary report on patentability PCT/US2012/024184, issued on Aug. 13, 2013, Rapiscan Systems Inc.
International Search Report PCT/US2012/024184, mailed on Jul. 27, 2012, Rapiscan Systems Inc.
International Search Report PCT/US2012/042493, mailed on Oct. 1, 2012, Rapiscan Systems Inc.

\* cited by examiner
† cited by third party

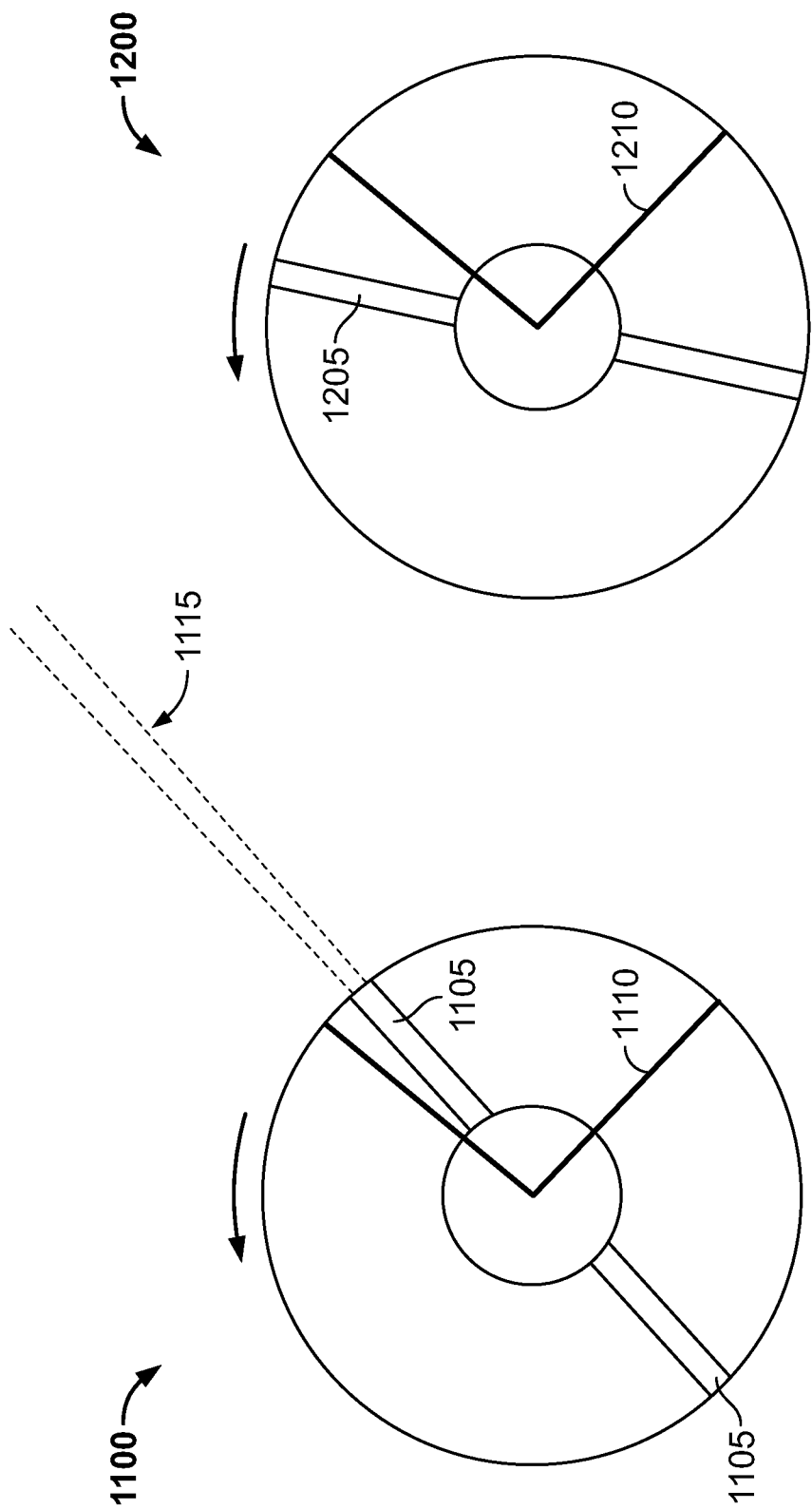

COVERT SURVEILLANCE USING MULTI-MODALITY SENSING

CROSS-REFERENCE TO RELATED APPLICATIONS

The present specification is a continuation of U.S. patent application Ser. No. 13/523,604, of the same title, filed on Jun. 14, 2012, which, in turn, relies on U.S. Provisional Patent Application No. 61/497,024, of the same title, and filed on Jun. 14, 2011, for priority and is incorporated herein by reference in its entirety.

The present specification is also a continuation-in-part of U.S. patent application Ser. No. 13/368,202, entitled "Covert Surveillance Using Multi-Modality Sensing", and filed on Feb. 7, 2012, which relies on U.S. Provisional Patent Application No. 61/440,834, of the same title and filed on Feb. 8, 2011, for priority. The aforementioned application is incorporated herein by reference in its entirety.

The present invention also relies on U.S. patent application Ser. No. 12/916,371, entitled "Mobile Aircraft Inspection System" and filed on Oct. 29, 2010, for priority, which is herein incorporated by reference in its entirety.

FIELD

The present specification generally relates to the field of covert surveillance for detecting threat items and contraband, either in a vehicle or on a person, and more specifically to a covert mobile inspection vehicle which combines a plurality of detection and prevention components that may be deployed rapidly to a threat zone to aid detection and prevention of subversive activities. More specifically, the present specification relates to an inspection system and method for simultaneous active backscatter and passive radiation detection.

BACKGROUND

To counter the threat of terrorism, there is a requirement for systems to be put in place to detect and address subversive activity. Some of such systems known in the art are purely designed to detect subversive activity; others are designed to prevent subversive activity; while still other known systems are designed purely as a deterrent. For example, some systems are primarily physical (such as barriers and security agents), some rely on networks of sensors (such as CCTV systems) while others involve dedicated installations (such as radio jamming mast or X-ray scanning machines).

What is needed, however, are covert surveillance systems that are highly mobile, can be rapidly deployed and allow the use of a plurality of surveillance data to enable more informed, robust and intelligent threat detection and prevention.

Accordingly, there is need for a covert mobile inspection vehicle that uses a plurality of prevention and detection components or sensors.

There is also need for a system that intelligently integrates and/or correlates surveillance information from the plurality of multi-modality sensors to detect and prevent subversive activities.

Further, among detection systems that provide for efficient non-invasive inspection, X-ray imaging systems are the most commonly used. Transmission based X-ray imaging systems are traditionally used to inspect trucks and cargo containers for contraband. Inspection of a certain larger structures, such as complete aircraft, however, can be challenging with a transmission-based geometry wherein, typically, the source is located on one side of the aircraft and detectors are located on the other side of the aircraft. This geometry has many challenges, and in particular, when scanning around the landing gear and engines there is difficulty in placing detectors and thus, in producing radiographic images.

In backscatter-based inspection systems, X-rays are used for irradiating a vehicle or object being inspected, and rays that are scattered back by the object are collected by one or more detectors. The resultant data is appropriately processed to provide images which help identify the presence of contraband. Since aircraft are typically made of lighter materials, a backscatter-based detection system would provide adequate penetration in most cases and thus would only require equipment to be placed on one side of the aircraft.

However, backscatter technology may not be suitable when all areas of the aircraft have to be penetrated with a high detection probability, such as is the case with nuclear materials detection. Areas of high attenuation as measured by the backscattered radiation include fuel tanks, transformers, counterweights, among other aircraft components. In addition, backscatter technology cannot effectively discriminate between typical metals and special nuclear materials.

Aircraft inspection calls for unique requirements such as the capability of inspecting large aircraft from more than one side. In addition, varying aircraft sizes would require the inspection head to scan at different heights, and several sections of the aircraft, such as the wings and tails, would require different head and detector scanning configurations. Conventional X-ray backscatter and transmission systems, however, do not have adequate scanning robustness, ability to work in various orientations, scanning range, or field of view for aircraft inspection applications.

There is also a need to detect partially shielded or unshielded special and radiological materials using passive detection technology.

There is an even greater need to perform active and passive measurements simultaneously to prevent re-scanning the object or to avoid having two separate screening systems.

In passive radiation-based detection systems, radiation emitted from special and radiological materials is measured without active interrogation. It is challenging, however, to combine both active backscatter inspection and passive radiation detection while still ensuring that the backscatter beam signals do not interfere with passive detection techniques, because the high backscatter radiation will impinge upon passive detectors at the same time the low-intensity passive signals are measured.

Therefore, what is needed is a method and system for detection of both active backscatter and passive radiation, and in particular, simultaneous inspection.

What is also needed is an active and passive detection system that is easily transportable, mobile, and non-intrusive, that is capable of operating even in rugged outdoor conditions such as airport environments.

SUMMARY

In one embodiment, the present specification discloses a covert mobile inspection vehicle comprising: a backscatter X-ray scanning system comprising an X-ray source and a plurality of detectors for obtaining a radiographic image of an object outside the vehicle; at least one sensor for determining a distance from at least one of the plurality of detectors to points on the surface of the object; a processor for processing the obtained radiographic image by using the determined distance of the object to obtain an atomic number of each material contained in the object; and one or more sensors to obtain surveillance data from a predefined area surrounding the vehicle. In an embodiment, the sensor is a scanning laser range finder causing a beam of infra-red light to be scattered from the surface of the object wherein a time taken for the beam of infra-red light to return to the sensor is indicative of the distance to the surface of the object.

In one embodiment, the present invention is an inspection system and method for simultaneous active backscatter and passive radiation detection.

In one embodiment, the present invention is a simultaneous low energy backscatter (100-600 kV) and passive radiation (gamma rays and neutrons) detection system and method.

In one embodiment, the present invention is a non-intrusive inspection system that includes an inspection head having an x-ray source, a scanning wheel, a dual-purpose detector and associated electronics. The dual purpose detector can detect both backscatter x-rays and passive radiation. In one embodiment, the x-ray and gamma ray detectors are combined in the same module. In another embodiment, the x-ray detector is different from the gamma-ray detector.

In one embodiment, the x-ray source of the present invention is constantly on, producing x-rays in a fan beam. In one embodiment, a spinning wheel having a plurality of pinholes therein is employed to produce a pencil beam of radiation through at least one pinhole. In one embodiment, the spinning wheel is employed to "block" the x-ray fan beam (and resultant pencil beam) from exiting, by blocking the slits in the spinning wheel, during which time passive radiation detection is active.

In another embodiment, a beam chopping mechanism is employed, wherein the beam chopping mechanism is designed to present a helical profile shutter (aperture), formed on a cylinder, for X-ray beam scanners. In one embodiment, a radiation shield is provided on a radiation source such that only a fan beam of radiation is produced from the source. The fan beam of radiation emits X-rays and then passes through the spin-roll chopper, which acts as an active shutter. Thus, when the spin-roll chopper and therefore, helical aperture(s) is rotating, there is only a small opening for the X-ray fan beam to pass through, which provides the moving flying spot beam. In this embodiment, at least one gap between the spin-roll slits is used to block the exiting radiation to allow for passive measurements.

In yet another embodiment, a scanning pencil beam is generated by any one of the approaches described above or any other approach as is known to those of ordinary skill in the art and deactivated by turning off the X-ray source (in contrast with previous embodiments, where the source is "blocked" by use of the spinning wheel or spin-roll chopper). Examples of suitable x-ray sources include, but are not limited to gridded sources, field emission electron sources (e.g. carbon nanotubes) or any other source that can switch the beam on-off within a few microseconds.

In one embodiment, the present invention is a system for detecting concealed threats in an object by simultaneously performing active and passive radiation detection, the system comprising: an X-ray source with a modulating device to produce a pencil beam of radiation for scanning the object, said modulating device capable of blocking the pencil beam at regular intervals; a detector module for detecting both radiation backscattered by the object when scanned with the pencil beam of radiation and passive radiation emitted from threats within said object when the pencil beam of radiation is blocked, wherein said detector module comprises at least one detector; and a controller to measure backscattered radiation only when the x-ray pencil beam is on, and to measure only passive radiation when the x-ray pencil beam is blocked.

In another embodiment, the present invention is a system for detecting concealed threats in an object by simultaneously performing active and passive radiation detection, the system comprising: an X-ray source with a modulating device to produce a pencil beam of radiation for scanning the object; a controller for switching the X-ray source on and off at regular intervals; and a detector module comprising an X-ray detector for detecting radiation backscattered by the object when scanned with the pencil beam, and a passive radiation detector for detecting radiation emitted from threats inside said object when the pencil beam is switched off. The system further comprises control electronics to measure backscattered radiation only when the beam is on, and to measure only passive radiation when the x-ray pencil beam is off.

In one embodiment, the detector module comprises a detector array, wherein said detector array is capable of detecting both backscattered x-rays and passive radiation. In one embodiment, the passive radiation detector is at least one of a gamma ray detector, a neutron detector, or a gamma-neutron detector. In one embodiment, the neutron detector is used to passively measure neutrons simultaneously with backscatter radiation and passive gamma rays.

In one embodiment, the modulating device comprises a disc with at least one pinhole. In another embodiment, the modulating device comprises a cylindrical chopper with at least one helical slit. In one embodiment, the modulating device is rotated to produce a pencil beam that is blocked at regular intervals and the system does not illuminate the object with radiation when the pencil beam is blocked.

In one embodiment, the X-ray source is switched on and off at least once in a time period determined by a rotational frequency of the X-ray source, on the order of less than 1% of the rotational time.

In another embodiment, the present invention is a method for detecting concealed threats in an object by simultaneously performing active and passive radiation detection, the method comprising: modulating an X-ray source to produce a pencil beam of radiation for scanning the object, such that the pencil beam is blocked at regular intervals; and detecting radiation backscattered by the object when scanned with the pencil beam, and detecting passive radiation emitted from threats inside said object when the pencil beam is blocked. In one embodiment, radiation is detected by using a dual-purpose detector adapted to detect both backscattered x-rays and passive radiation. In another embodiment, passive radiation is detected using a separate passive radiation detector that is at least one of a gamma ray detector, a neutron detector, or a combined gamma-neutron detector. In one embodiment, the neutron detector passively measures neutrons simultaneously with backscatter radiation and passive gamma rays.

In one embodiment, backscattered radiation is measured when the x-ray pencil beam is on, and only passive radiation is measured when the beam is blocked. In one embodiment, the X-ray beam is modulated using a modulating device that comprises a disc with at least one pinhole. In another embodiment, the beam is modulated using a modulating device that comprises a cylindrical chopper with helical slits. In one embodiment, the modulating device is rotated to produce a pencil beam and is adapted to block said pencil beam at regular intervals. In one embodiment, the measured backscatter radiation and passive radiation data is combined to determine the presence of threats.

In yet another embodiment, the present invention is a system for detecting concealed threats in an object by simultaneously performing active and passive radiation detection, the system comprising: an X-ray source with a modulating device to produce a pencil beam of radiation for scanning the object; a detector module comprising a detector for detecting radiation backscattered by the object when scanned with the pencil beam and radiation emitted from threats inside said object; and control electronics to measure a resultant backscatter signal having energies less than a first threshold and to measure passive gamma rays above a second threshold that is set at approximately the first threshold. In one embodiment, the system further comprises a processor, wherein said processor is programmed to subtract background noise produced by the high-energy gamma rays from the backscatter signal. In one embodiment, the system comprises a neutron detector to passively measure neutrons simultaneously with the backscatter radiation and passive gamma rays. In one embodiment, a processor is employed to analyze both the x-ray image and the passive gamma and neutron information for potential threats.

The aforementioned and other embodiments of the present shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 11 is an illustration of one embodiment of a spinning wheel as used in the system of the present invention, showing the pencil beam in an "on" position, wherein a backscatter measurement is taken;

FIG. 12 is an illustration of one embodiment of a spinning wheel as used in the system of the present invention, showing the pencil beam in an "off" position, wherein a passive measurement is taken;

DETAILED DESCRIPTION

Figure 1A:
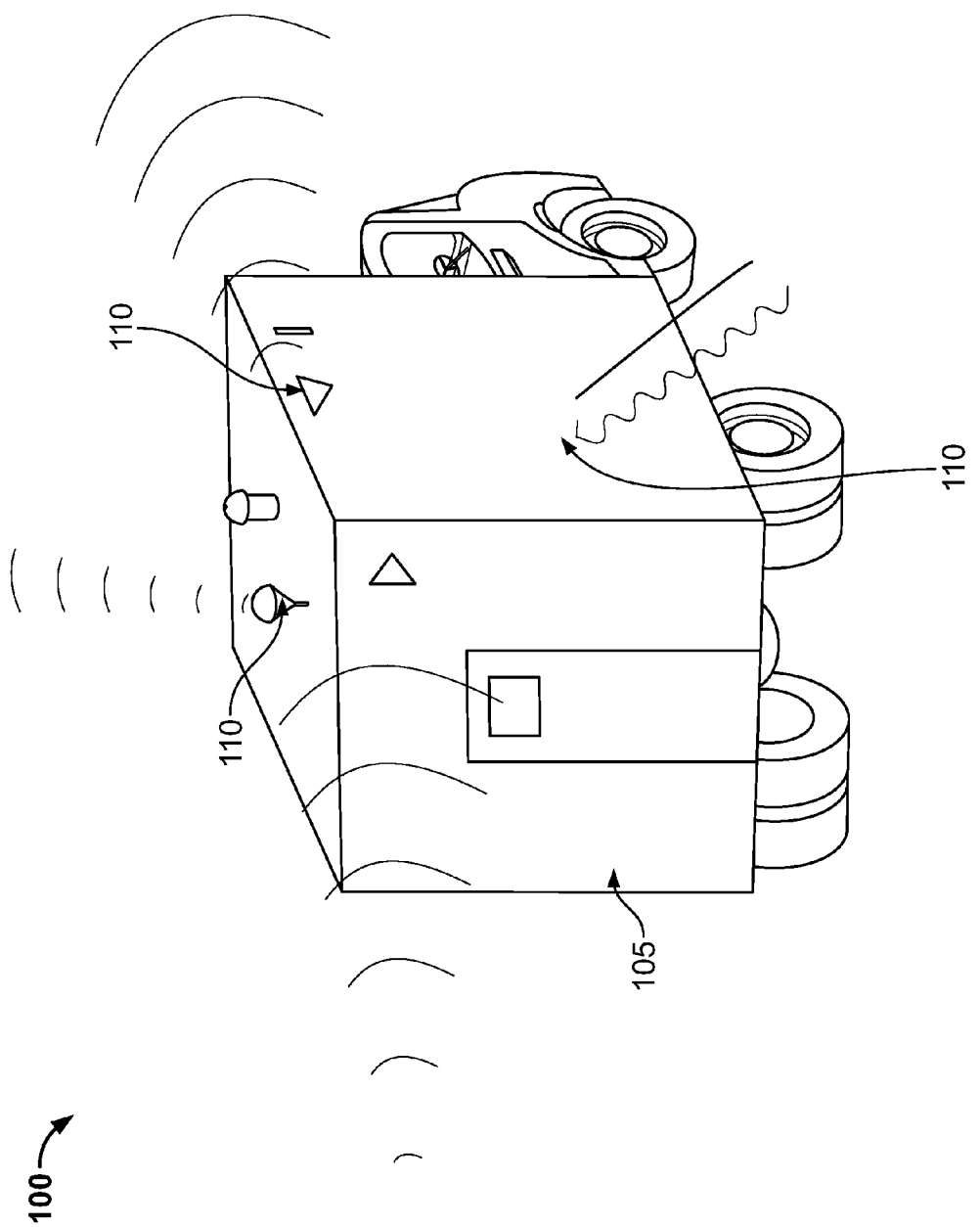
FIG. 1A is an illustration of a covert mobile inspection vehicle, in accordance with an embodiment of the present invention.

The present specification is directed towards a covert mobile inspection system, comprising a vehicle, which is equipped with a plurality of multi-modality sensors. Surveillance information from the plurality of sensors is utilized to detect and prevent subversive activities. Thus, the present specification describes a system and method for providing covert and mobile surveillance/inspection of subversive activities using a plurality of multi-modality surveillance sensors.

In addition, the present specification is directed toward using a backscatter X-ray scanning system that has improved threat detection capabilities as at least one of the plurality of surveillance sensors utilized.

Accordingly, in one embodiment, the present specification describes a covert mobile inspection vehicle having an improved on-board backscatter X-ray scanning system and further equipped with a plurality of prevention and inspection components or devices.

In one embodiment, the backscatter X-ray scanning system includes a sensor, such as a scanning laser range finder, that measures the distance of the detectors from the surface of the object under inspection.

Because it is possible to map the equivalent distance between the X-ray beam at any angle and the surface of the object by determining the relative positions of the X-ray source and the laser sensor, in one embodiment, the present specification describes an improved method of generating a radiographic image of the object under inspection, using this known distance to generate an intensity-corrected image at a given equivalent distance. The corrected image is then used to map an effective atomic number of all materials in the radiographic image. Additionally, this distance data is also used to provide an accurate geometric correction in the image to produce a true likeness of the shape of the object under inspection.

In another aspect of the improved method of generating a radiographic image of the object under inspection, adaptive region based averaging is applied (such as by using a statistical filter and/or median filter). This results in an image which has equivalent statistical properties useful in determining an accurate effective atomic number for all regions in the object under investigation. Optionally, the knowledge of effective atomic numbers and their ranges or variations is used to colour code the radiographic image.

In another embodiment, the present specification describes a method for measuring individual X-ray energies as they interact within at least one detector in order to form an analysis of the spectral content of the scattered X-ray beam.

In another embodiment, the backscatter X-ray scanning system additionally uses a multi-element scatter collimator to allow use of fan-beam X-ray irradiation to generate the backscatter image. Therefore, scattered X-rays which lie within an acceptance angle of, for example, the collimator element are detected and associated to the appropriate corresponding part of the generated radiographic X-ray image.

Apart from the X-ray scanner/sensor, the plurality of multi-modality surveillance sensors comprise any or all combinations of components such as GPS receivers, scanning lasers, CCTV cameras, infra-red cameras, audio microphones, directional RF antennas, wide-band antennas, chemical sensors, jamming devices.

In accordance with another embodiment, the present specification describes an automated detection processor for integrating and analysing all surveillance information from the plurality of sensors, in real-time, to highlight threat items for review by an operator seated inside the covert vehicle and/or remotely through a secured wireless network.

The present specification discloses multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1A shows a covert mobile inspection system 100 in accordance with an embodiment of the present invention. The system 100 comprises a relatively small vehicle 102, such as a van, which is equipped with a plurality of detection and prevention sensors 104 such as scanning, listening and broadcasting devices. In an embodiment, the vehicle is a 3.5 ton chassis having a height less then 3 m above road level, length ranging from 4 m to 6 m and width ranging from 2.2 m to 2.5 m. In other embodiments, the vehicle may comprise small vans having a weight ranging from 1.5 T to 3.5 T. One aspect of the embodiments disclosed herein is the use of surveillance data from these multi-modality sensors in correlation and/or aggregation with data from an on-board X-ray scanning sensor. In one embodiment of the present invention, the X-ray scanning system on-board the surveillance vehicle of FIG. 1A also comprises a sensor in order to measure its distance to the scattering object, material or point.

In one embodiment, the X-ray sensor generates a backscatter radiographic image of an object from a single side utilizing Compton scattering. This allows the vehicle 105 to collect scan data, in a covert fashion, at a low dose to allow scanning of individuals, small as well as large vehicles/cargo for detection of threat devices, materials and individuals.

In another embodiment, the X-ray scanning system allows for scanning of several sides of a vehicle under inspection. For example, U.S. patent application Ser. No. 12/834,890 and Patent Cooperation Treaty (PCT) Application Number US10/41757 both entitled "Four-Sided Imaging", and filed on Jul. 12, 2010 by the Applicant of the present specification, both herein incorporated by reference in their entirety, describe "[a] scanning system for the inspection of cargo, comprising: a portal defining an inspection area, said portal comprising a first vertical side, a second vertical side, a top horizontal side, and a horizontal base defined by a ramp adapted to be driven over by a vehicle; a first X-ray source disposed on at least one of the first vertical side, second vertical side or top horizontal side for generating an X-ray beam into the inspection area toward the vehicle; a first set of transmission detectors disposed within the portal for receiving the X-rays transmitted through the vehicle; a second X-ray source disposed within the ramp of said portal for generating an X-ray beam towards the underside of the vehicle; and a second set of detectors disposed within the ramp of said portal for receiving X-rays that are backscattered from the vehicle.

Figure 1B:
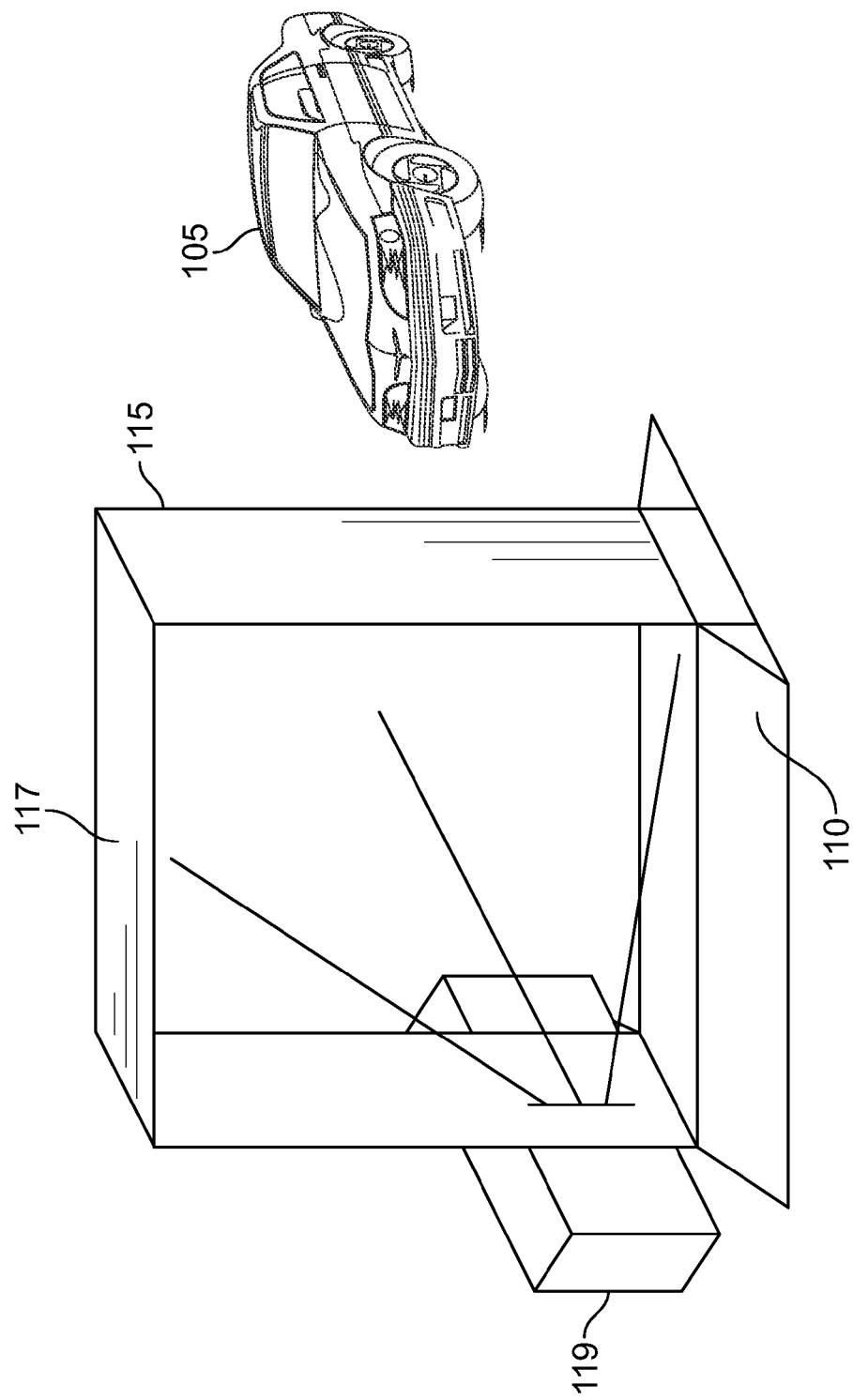
FIG. 1B is a schematic representation of one embodiment of a four-sided X-ray imaging system that may be employed in accordance with the present invention.

FIG. 1B is a schematic representation of one embodiment of the four-sided X-ray imaging system 100B disclosed in U.S. patent application Ser. No. 12/834,890 and Patent Cooperation Treaty (PCT) Application Number US10/41757. As shown in FIG. 1B, vehicle 105 drives over a ramp 110 and underneath an archway 115, which defines an inspection portal. Specifically, the portal is defined by a first (left) side, a second (right) side, a top side and a bottom platform, which is a portion of the ramp 110. In one embodiment, ramp 110 comprises a base, a first angled surface leading upward to a flat transition point defining the highest part of the ramp, which also functions as the bottom platform, and a second angled surface leading back down to the ground. The highest part of the ramp is typically between 50 and 150 mm in height. In one embodiment, archway 115 houses multiple X-ray transmission detectors 117 and at least one X-ray source 119, housed within an enclosure, shown as 220 in FIG. 2.

While FIG. 1B depicts the X-ray source 119 as being on the left side of the portal, one of ordinary skill in the art would appreciate that it could be on the right side, with an appropriate reconfiguration of the detectors 117. Preferably, the enclosure housing the X-ray is physically attached to the exterior face of the first side and is approximately 1 meter tall. The position of the enclosure depends upon the size of the inspection portal. In one embodiment, the enclosure occupies 20% to 50% of the total height of the first side. In one embodiment, a slit or opening is provided on first side, through which X-rays are emitted. Slit or opening extends substantially up first side to approximately 100% of the height. In one embodiment, slit or opening is covered with a thin coating that is substantially transparent to an X-ray. In one embodiment, the thin coating is comprises of a material such as aluminium or plastic and further provides an environmental shield.

In one embodiment, the enclosure and X-ray unit further comprise a first collimator close to the source of X-rays and a second collimator close to the exit, described in greater detail below. Where the X-ray source enclosure is so positioned, detectors 117 are positioned on the interior face of the second side and the interior face of top side and occupy the full height of second side and the full length of top side, proximate to second side.

In another embodiment, the enclosure housing the X-ray is physically attached to the exterior face of the second side and is approximately 1 meter tall. The position of the enclosure depends upon the size of the inspection portal. In one embodiment, the enclosure occupies 20% to 50% of the total height of the first side. As described above with respect to first side, if the enclosure housing the X-ray is on second side, a slit or opening is similarly provided on second side. The detectors are also similarly positioned on the interior faces of top side and first side when the enclosure is on second side. In one embodiment, with a dual-view system, an enclosure housing an X-ray source can be provided on both the first side and second side.

Figure 2:
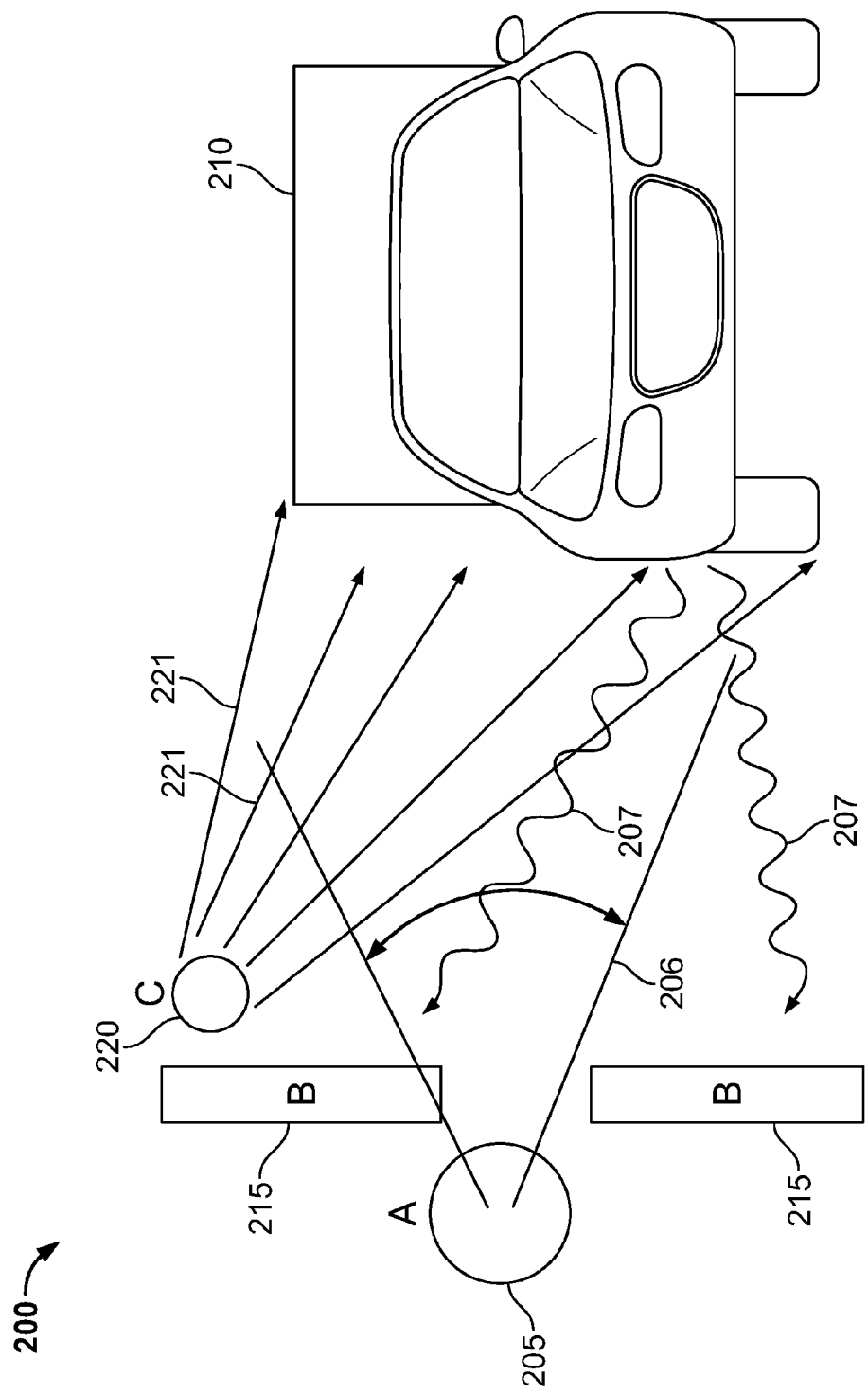
FIG. 2 is an illustration of an embodiment of the X-ray scanning system on-board the surveillance vehicle of FIG. 1A in accordance with one embodiment of the present invention.

As shown in FIG. 2, the X-ray scanning system 200 comprises an X-ray source 205 collimated by a rotating disk with a small aperture which allows X-rays to scan in at least one pencil beam 206, and preferably a series of "moving" pencil beams, within a substantially vertical plane from the X-ray source 205 to the object 210. X-rays 207 scatter back from the object 210 under inspection and some of these reach at least one detector array 215 located adjacent to the X-ray source 205 but outside the plane described by the moving X-ray beam 206. The intensity of the backscatter signal 207 is representative of the product of distance to the object and atomic number of the object.

Persons of ordinary skill in the art would appreciate that the signal size due to Compton scattering from objects varies as the inverse fourth power of distance between the X-ray source and the scattering object. It is also known to persons of ordinary skill in the art that low atomic number materials are less efficient at scattering X-rays than high atomic number materials while high atomic number materials are more efficient at absorbing X-rays of a given energy than low atomic number materials. Therefore, the net result is that more X-rays having a greater intensity are scattered from low atomic number materials than from high atomic number materials. However, this effect varies approximately linearly with atomic number while the X-ray signal varies as the inverse fourth power of distance from the source to the scattering object. This also implies that known Compton scatter based radiographic images are essentially binary in nature (scattering or not scattering) since the small but quantitative variation of the signal size due to variation in atomic number is lost in the gross variation in signal intensity caused due to varying distances from X-ray source to scattering points.

To correct for distance, a sensor 220 is provided (adjacent to the X-ray source and detectors) which is capable of detecting the distance to each point at the surface of the object 210. In one embodiment, the sensor 220 is advantageously a scanning laser range finder in which a beam of infra-red light 221 is scattered from the surface of the object 210 and the time taken for the pulsed beam to return to the sensor 220 is indicative of the distance to the surface of the object 210. For example, U.S. patent application Ser. No. 12/959,356 and Patent Cooperation Treaty Application Number US10/58809, also by the Applicant of the present specification, entitled "Time of Flight Backscatter Imaging System" and filed on Dec. 22, 2010, both of which are herein incorporated by reference in their entirety, describes a method in which the time of flight of the X-ray beam to and from the surface of the object under inspection is used to determine the distance between the source and scattering object.

One of ordinary skill in the art would note that the distances between the surface of the object and the planar detector arrays are variable, since the object is not straight sided. Further, since the distance from the X-ray source to the object under inspection is not known in general, an assumption is generally made that the object is planar and at a fixed distance from the source. Thus, if the object is closer than assumed, then the object will appear smaller in the image and conversely, if the object is further away then it will appear to be larger. The result is an image which is representative of the object under inspection but not with correct geometry. This makes it difficult to identify the precise location of a threat or illicit object within the object under inspection.

U.S. patent application Ser. No. 12/959,356 and Patent Cooperation Treaty Application Number US10/58809 address the above problem by integrating time of flight processing into conventional backscatter imaging. X-rays travel at a constant speed which is equal to the speed of light ($3 \times 10^8$ m/s). An X-ray will therefore travel a distance of 1 m in 3.3 ns or equivalently, in 1 ns ($10^{-9}$ s) an X-ray will travel 0.3 m. Thus, if the distance between a backscatter source and the object under inspection is on the order of 1 m, it corresponds to around 3 ns of transit time. Similarly, if the backscatter X-ray detector is also located around 1 m from the surface of the object, it corresponds to an additional 3 ns of transit time. Thus, the signal received at the detector should be received, in this example, 6 ns after the X-ray beam started its transit from the X-ray tube. In sum, the X-ray's transit time is directly related to the detectors' distance to or from the object. Such times, although quite short, can be measured using detection circuits known to those of ordinary skill in the art.

The minimum distance is practically associated with the time resolution of the system. Objects can be proximate to the source, but one will not see much scattered signal since the scatter will generally be directed back to the X-ray source rather than to a detector. A practical lower limit, or the minimum distance between the plane of the system and the nearest part of the object to be inspected, is 100 mm. The further away the object is from the detector, the smaller the signal size and thus a practical upper limit for distance is of the order of 5 m.

Figure 2A:
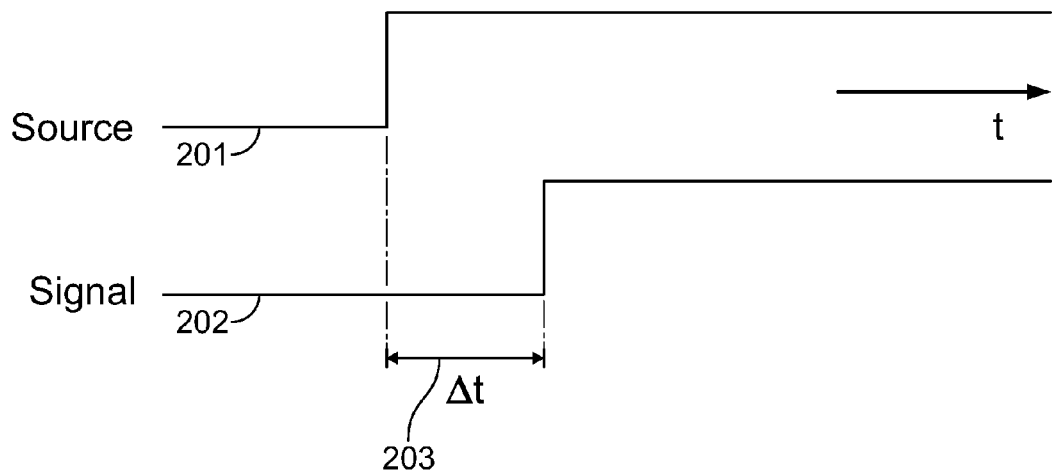
FIG. 2A depicts a representation, as a step function, of an X-ray source being switched rapidly from its beam-off condition to its beam-on condition, that may be employed in accordance with the present invention.
Figure 2B:
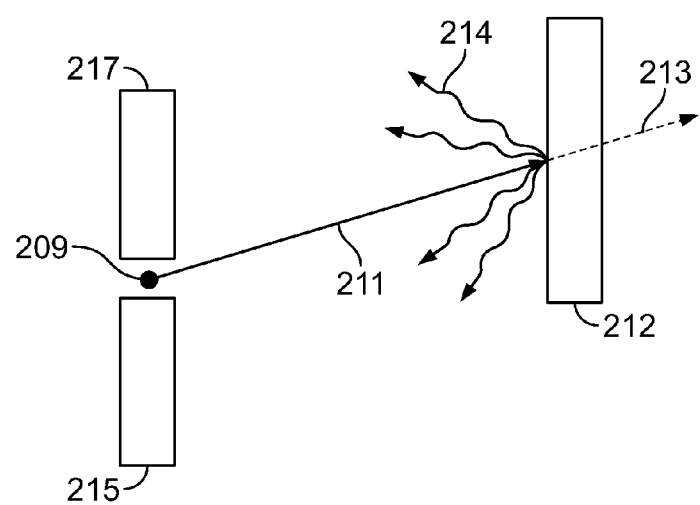
FIG. 2B diagrammatically illustrates an operation of time of flight backscatter imaging, that may be employed in accordance with the present invention.

In the systems of the present application, as shown diagrammatically in FIGS. 2A and 2B, the distance between the X-ray source and the object under inspection is determined precisely by recording the time taken for an X-ray to leave the source and reach the detector. FIG. 2A depicts a representation, as a step function, of an X-ray source being switched rapidly from its beam-off condition to its beam-on condition. While 201 represents the step function at the source, 202 represents the detector's response. Thus, as can be seen from 201 and 202, after the beam is switched on from its off state at the source, the detector responds with a step-function like response after a time delay $\Delta t$ 203. Referring to FIG. 2B, as the source 209 emits a pencil beam 211 of X-rays towards the object 212, some of the X-rays 213 transmit into the object 212, while some X-rays 214 backscatter towards the detectors 217.

It may be noted that there are different path lengths from the X-ray interaction point (with the object) to the X-ray detector array. Therefore if a large detector is used, there will be a blurring to the start of the step pulse at the detector, where the leading edge of the start of the pulse will be due to signal from the part of the detector which is nearest to the interaction spot, and the trailing edge of the start of the pulse will be due to signal from parts of the detector which are further away from the interaction spot. A practical system can mitigate such temporal blurring effects by segmenting the detector such that each detector sees only a small blurring and the changes in response time each provide further enhancement in localisation of the precise interaction position, hence improving the determination of the surface profile of the object under inspection.

The detector size (minimum and/or maximum) that would avoid such blurring effects described above is commensurate with the time resolution of the system. Thus, a system with 0.1 ns time resolution has detectors of the order of 50 mm in size. A system with 1 ns time resolution has detectors of the order of 500 mm in size. Of course, smaller detectors can be used to improve statistical accuracy in the time measurement, but at the expense of reduced numbers of X-ray photons in the intensity signal, so there is a trade-off in a practical system design which is generally constrained by the product of source brightness and scanning collimator diameter.

Figure 3C:
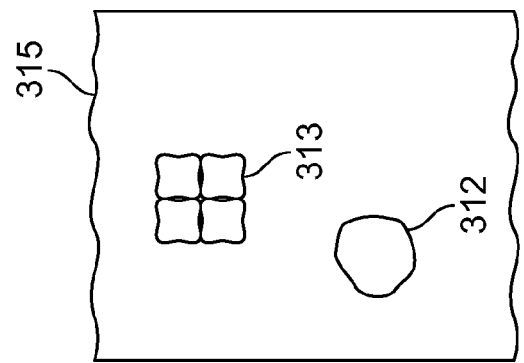
FIG. 3C depicts a backscatter radiographic quantitative image scaled by effective atomic number, in accordance with an embodiment of the present invention.

Referring to FIG. 2, it should be appreciated that knowing the relative positions of the X-ray source 205 and the laser sensor 220 the equivalent distance between the X-ray beam 206 at any angle and the surface of the object 210 is mapped using a geometric look up table (for computational efficiency). This known distance is then used to apply an intensity correction to the measured X-ray scatter data to produce a radiographic image at a given equivalent distance of, say, 1 m. Thus, objects that are closer than 1 m will have their intensity reduced by a factor of $1/(1\text{-distance})^4$ while objects farther away than 1 m will have their intensity increased by a factor of $1/(1\text{-distance})^4$. The quantitatively corrected image so produced is then used to map an effective atomic number of all materials in the radiographic image, as shown in FIGS. 3A through 3C.

Figure 3B:
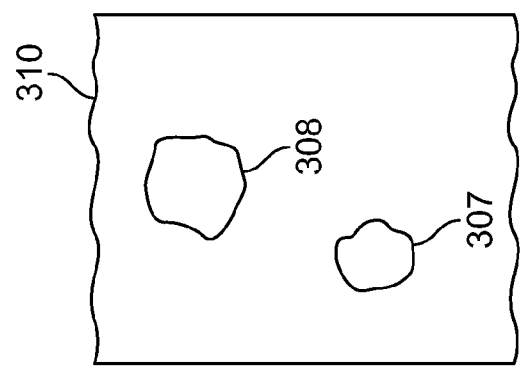
FIG. 3B depicts a backscatter radiographic image where intensity of object images has been scaled for distance, in accordance with an embodiment of the present invention.
Figure 3A:
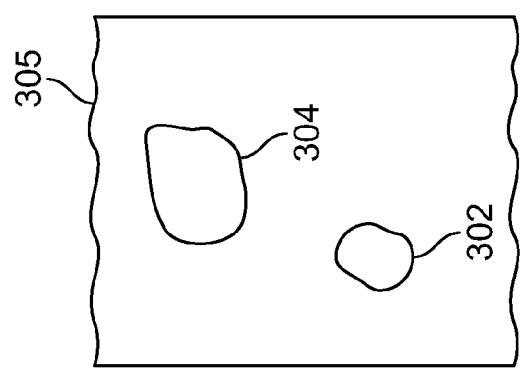
FIG. 3A depicts a backscatter radiographic image without using intensity or effective atomic number scaling.

As shown in FIG. 3A, radiographic image 305 represents an image of two objects obtained using an X-ray scanning system without intensity or effective atomic number scaling, the lower one 302 being close to the X-ray source and the upper one 304 being farther away from the source. The lower object 302 is shown to be bright while the upper image 304 is seen to be faint.

Referring now to FIG. 3B, image 310 shows the result of scaling intensity for distance where the lower object 307 is now lighter than in image 305 while the upper object 308 is now brighter than the lower object 307. This suggests that the upper object 308 is of lower atomic number than the lower object 307. This is in contrast to the original image 305, wherein the relative atomic numbers are typically prone to misrepresentation.

In accordance with another aspect of the present application, it is recognized that signal scattered due to objects farther from the X-ray source have poorer signal-to-noise ratio than signal from scattering objects closer to the source. This implies that the distance measurement can be further utilized to implement an adaptive region based averaging method whereby signal from regions far from the source are averaged over a larger region, such that the linear dimension of these regions is scaled as the square of the distance from source to object. This effect is shown in image 315 of FIG. 3C. In FIG. 3C, the upper object 313 has been averaged over larger regions than the lower object 312 thereby resulting in equivalent statistical properties useful in determining an accurate effective atomic number for all regions in the object under investigation. In a preferred embodiment, the adaptive region averaging method is implemented using a statistical filter to determine if a given pixel is likely to be a part of the main scattering object, or part of an adjacent object in which this value should not be used to compute the region average.

In one embodiment, a suitable statistical filter lists all pixel values within a region (for example a 7×7 block), ranks them in order and then determines the mean value and standard deviation of the central range of values. Any pixel within the whole block whose intensity is more than 2 standard deviations from the mean value within that block is considered to be part of an adjacent object. A range of statistical filters can be developed which may use higher order statistical attributes, such as skewness, to refine the analysis. Alternate methods, such as median filtering, which can mitigate against boundary effects between image features are well known to persons of ordinary skill and all such methods can be suitably applied within the scope of the present invention.

In accordance with yet another aspect described in the present specification, in one embodiment, the individual pixels in image 310 are colored according to the values in the quantitative image 315 scaled by effective atomic number. Here, the distance normalized pixels are colored on an individual basis (to ensure a sharp looking image) based on results from the region averaged image 315 with improved statistics. Alternative schemes can also be used for pixel coloring. For example, pixels with effective atomic number below 10 are colored orange (corresponding to organic materials such as explosives), pixels with effective atomic numbers between 10 and 20 are colored green (corresponding to low atomic number inorganic materials such as narcotics) while materials with effective atomic numbers greater than 20, such as steel, are colored blue. Still alternatively, a rainbow spectrum can be used in which pixel colored changes from red through yellow, green and blue as effective atomic number increases. Many other color tables can be selected depending on preference and application.

In accordance with further aspect of the present specification, it is recognized that the beam from the X-ray source is diverging from a point which is generally located at least one meter from ground level. This implies that the raw image 305 is actually distorted—with regions at the centre of the image being unnaturally wide compared to regions at the top and bottom of the image which are unnaturally narrow. In conventional methods, a geometric correction is applied according to a cosine-like function which makes the assumption of a flat sided object at a fixed distance from the source. In contrast, in an embodiment of the present invention, the distance data from the scanning laser sensor 220 of FIG. 2 is used to provide an accurate geometric correction to produce a true likeness of the shape of the object under inspection.

Figure 4:
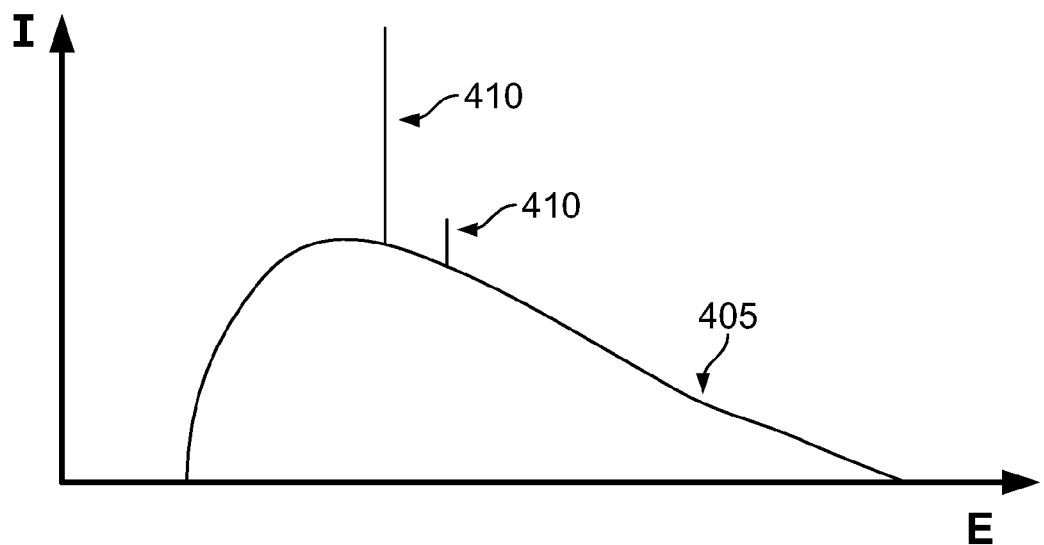
FIG. 4 is a graphical representation of a Bremsstrahlung spectrum with a typical tungsten anode X-ray tube.

The present invention also lays focus on spectral composition of the X-ray beam that is incident on the object under inspection. Accordingly, in one embodiment it is advantageous to create the X-ray beam using an X-ray tube with cathode-anode potential difference in the range 160 kV to 320 kV with tube current in the range of 1 mA to 50 mA depending on allowable dose to the object under inspection and weight and power budget for the final system configuration. Regardless of tube voltage and current, a broad spectrum of X-ray energies is produced as shown in FIG. 4. Here, a broad Bremsstrahlung spectrum 405 is visible complimented by fluorescence peaks 410 at 60 keV with a typical tungsten anode tube.

Figure 5:
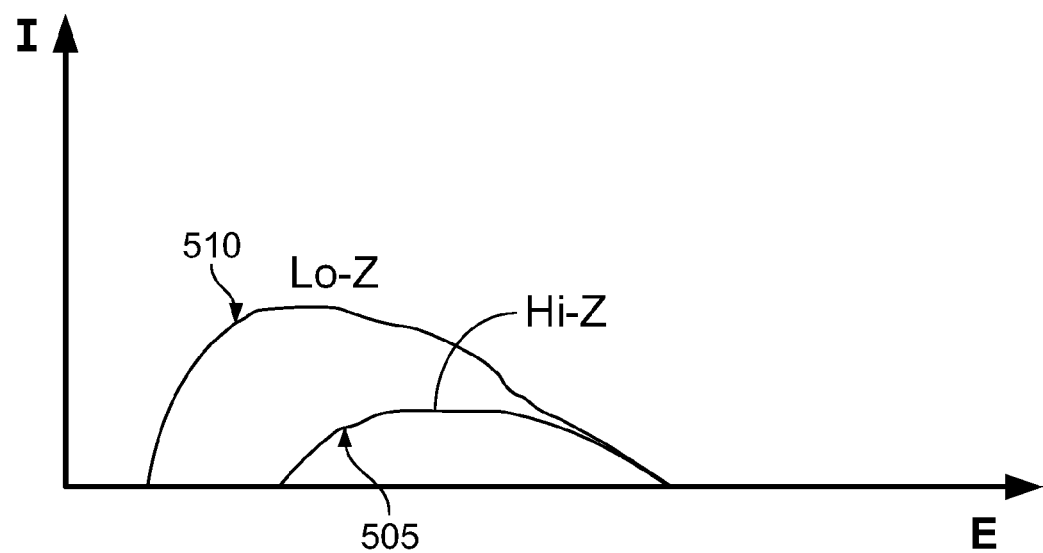
FIG. 5 is a graphical representation of a high mean energy spectrum for high Z materials and a low mean energy spectrum for lower Z materials, in accordance with an embodiment of the present invention.

It should be noted that as a result of Compton scattering, the X-rays backscattered towards the detectors are generally of lower energy than those interacting in the object itself, and so the scattered beam has a lower mean energy than the incident beam. Further, the impact of the scattering object is to preferentially filter the X-ray beam—removing more and more of the lower energy components of the beam the higher the effective atomic number of the scattering object. This phenomenon is shown in FIG. 5 where a high atomic number (Z) material represents higher mean energy spectrum 505 while a lower atomic number (Z) material is represented by the relatively lower mean energy spectrum 510, thereby enabling discerning of low Z items from relatively high Z items.

Referring back to FIG. 2, the detectors 215 measure the energy of the X-rays 207 that arrive at the detectors 215 after being scattered by the object 210. In one embodiment, each detector 215 comprises an inorganic scintillation detector such as NaI(Tl) or an organic scintillator such as polyvinyl toluene coupled directly to one or more light sensitive readout devices such as a photomultiplier tube or a photodiode. In an alternate embodiment, the detectors comprise semiconductor sensors such as semiconductors having a wide bandgap including, but not limited to, CdTe, CdZnTe or HgI which can operate at room temperature; or semiconductors having a narrow bandgap such as, but not limited to, HPGe which needs to be operated at low temperatures. Regardless of the detector configuration chosen, the objective is to measure individual X-ray energies as they interact in the detector in order to form an analysis of the spectral content of the scattered X-ray beam 207.

Persons of ordinary skill in the art would appreciate that the data acquisition module (typically comprising detectors, photomultipliers/photodiodes and analog-to-digital converter circuitry and well known to persons skilled in the art) will be synchronized to the position of the primary X-ray beam 206 in order to collect one spectrum for each interacting X-ray source point. For example, the X-ray system 200 may be configured to collect 300 lines per second with 600 pixels per image line. In this case, the equivalent dwell time of the primary X-ray beam at each source point is 1/180000 sec=5.5 µs per point and the detectors need to be capable of recording several hundred X-rays during this time. To achieve the necessary count rates, one embodiment uses a small number of fast responding detectors (such as polyvinyl toluene plastic scintillators with photomultiplier readout) or a larger number of slow responding detectors (such as NaI scintillators with photomultiplier readout), depending upon factors such as cost and complexity.

Given the acquisition of the X-ray spectrum at each sample point and the phenomena described with reference to FIGS. 4 and 5, it would be evident to those of ordinary skill in the art that the statistical properties of the X-ray spectrum can provide additional information on the effective atomic number of the scattering material at each primary beam interaction site. Using the known distance information, the area of the spectrum may be corrected to yield an improved quantitative result (as discussed earlier), while properties such as mean energy, peak energy and skewness of the spectrum provide the quantitative parameters that are required for accurate materials analysis.

As an example, a scattering object far from the detector will produce a naturally faint signal, with the displayed brightness of this object being corrected through the use of known distance information, such as that provided by a scanning laser. Given that the signal for the region is formed from a limited number of scattered X-ray photons, the properties of the signal can be described using Gaussian statistics. Gain correction to account for distance from the source is applied in a linear fashion, and so the region still maintains its original statistical properties even though its mean value has been scaled to a larger value.

Figure 7:
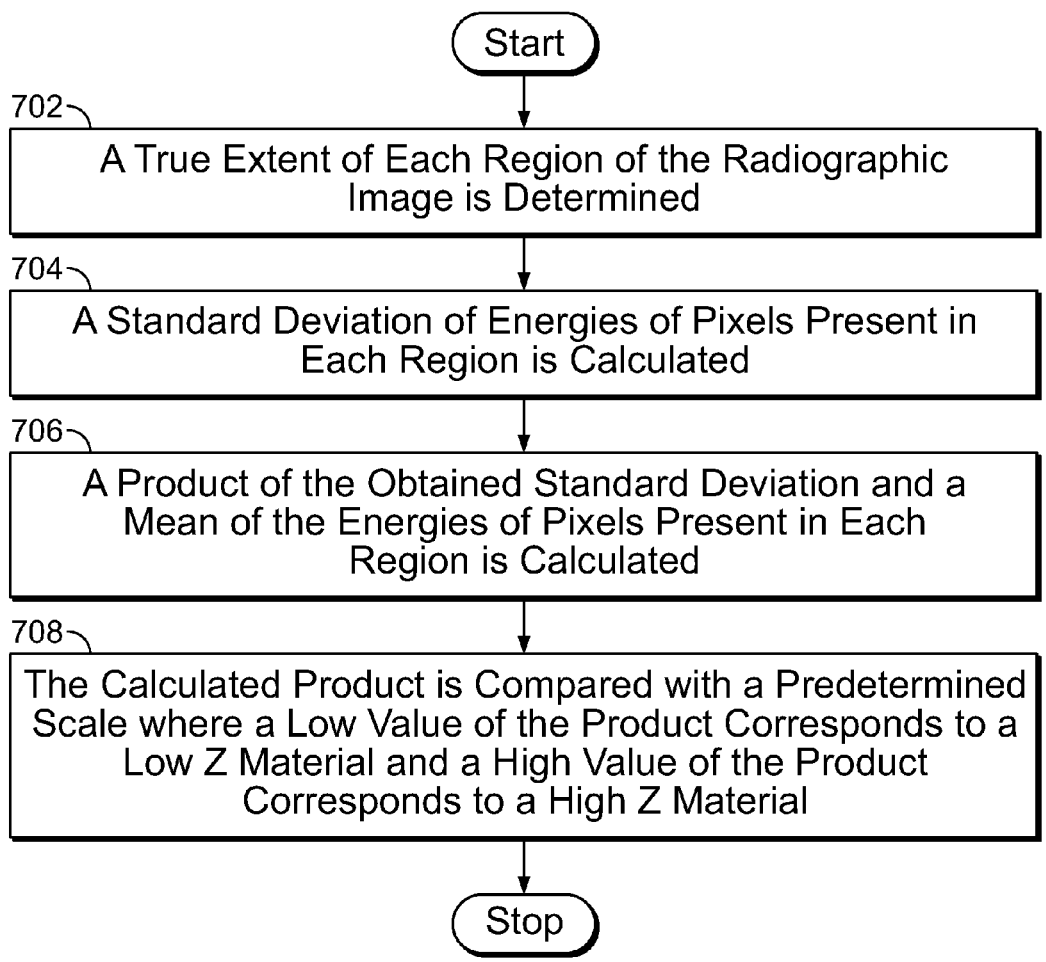
FIG. 7 is a flowchart illustrating a method of obtaining an atomic number of each material contained in an object being scanned by the covert mobile inspection vehicle of the present invention.

As identified in FIG. 5, the spectral composition of the scattered beam is dependent on effective atomic number of the scattering material. FIG. 7 is a flowchart illustrating a method of obtaining an atomic number of each material contained in an object being scanned by the covert mobile inspection vehicle of the present invention. At step 702, a true extent of each region of the radiographic image is obtained by using a suitable statistical filter as described earlier. A true extent of a region enables determining a boundary of each constituent material. Thus, the true extent refers to the physical area over which the object extends. It is desirable to find the point at which one object finishes and at which the next object begins so that only pixels for the current object are used in quantitative imaging, without the effects of contamination from adjacent objects. At step 704, a mean energy of each detected signal is calculated along with a standard deviation and skewness of energies of pixels present in each region. At step 706, a product of the calculated standard deviation and a mean energy of the pixels energies of pixels present in each region is calculated. At step 708, the calculated product is compared with a pre-determined scale where a low value of the product corresponds to a low atomic number material and a high value of the product corresponds to a high atomic number material.

In one embodiment, the present invention is directed towards a combination of active low-energy backscatter radiation (100-600 kV) detection and passive radiation (gamma rays and neutrons) detection for non-intrusive inspection of vehicles, trucks, containers, railcars, aircraft and other objects for nuclear, radiological and other contraband materials.

Figure 6:
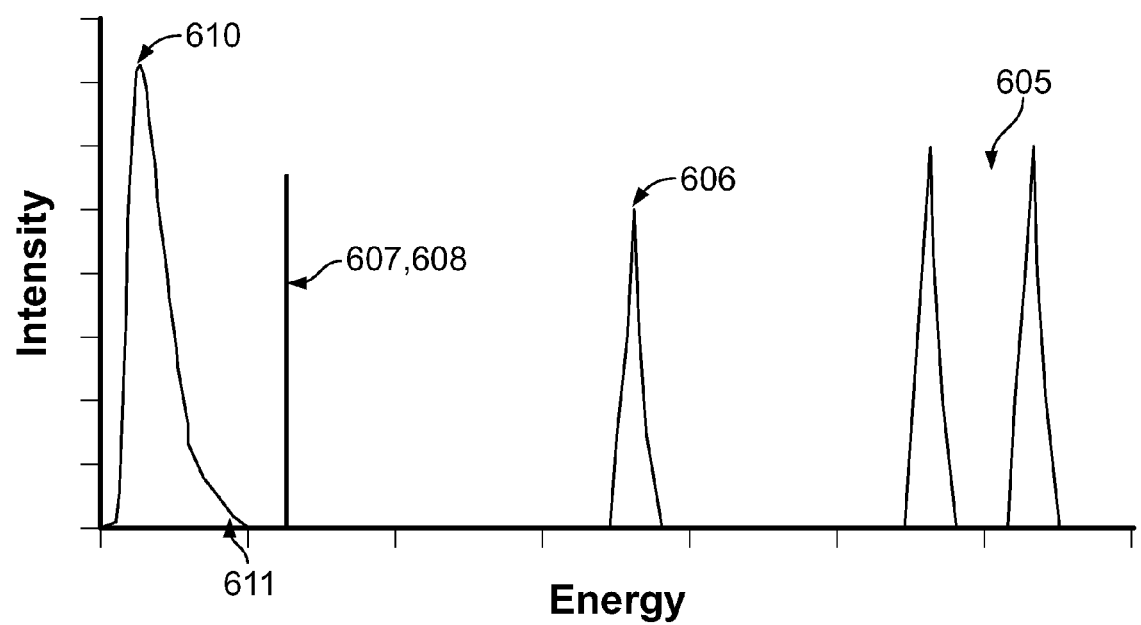
FIG. 6 is a graphical representation of a gamma ray spectrum with higher energies as compared with X-rays, in accordance with an embodiment of the present invention.

It should be appreciated that the X-ray scatter data is generally at low energy and often below 100 keV in magnitude. In contrast, gamma-rays from radioactive sources, that may be present in the object under inspection, will typically be at much higher energy (for example Co-60 has gamma-rays at 1.1 and 1.3 MeV while Cs-137 emits gamma rays at 662 keV). As shown in FIG. 6, it is therefore possible to discriminate these high energy gamma rays, represented by spectrums 605 and 606, from the low energy scattered X-rays 610 thereby allowing simultaneous acquisition of active X-ray backscatter signals along with passive gamma-ray detection in accordance with an aspect of the present invention.

In one embodiment, control electronics are employed to measure the resultant backscatter signal 610 having an upper threshold 611 set at or near the highest backscatter energy and to measure passive gamma rays 606, 605 above a threshold level 608 that is at or around the upper backscatter threshold 607.

It should be noted that the low-energy backscatter spectrum is contaminated with the Compton background produced in the detector from incomplete energy deposition. In general, this background is very low compared to the backscatter signal. However, if needed, this background can be subtracted based on the signals measured at high energy.

In one embodiment, the non-intrusive inspection system includes an inspection head having an x-ray source, a mechanism for producing a scanning pencil beam, a dual-purpose detector and associated electronics. The dual purpose detector can detect both backscatter x-rays and passive radiation.

In one embodiment, the x-ray source of the present specification is constantly on, producing x-rays in a fan beam. In one embodiment, a spinning wheel having a plurality of "slits" or "pinholes" therein is employed to "block" the x-ray fan beam (and resultant pencil beam) from exiting, during which time passive radiation detection is active.

In another embodiment, a beam chopping mechanism, such as a spin-roll chopper, is employed, wherein the beam chopping mechanism is designed to present a helical profile shutter (aperture), formed on a cylinder, for X-ray beam scanners. In this embodiment, the slits are configured in such a way that there is at least one gap where no pencil beam is produced and the beam is effectively turned "off".

In one embodiment, the present invention employs X-ray backscatter imaging, although one of ordinary skill in the art would appreciate that screening of the object may be performed using any available radiation imaging technique. For the purpose of inspection based on backscatter technology, in one embodiment the X-ray energy delivered by the source is optimized to be in the range of 150 kV to 600 kV. This range allows adequate penetration of the object under inspection. For better quality of imaging and to allow for shorter inspection times, the beam current is maximized, especially since the dose of radiation delivered to the object under inspection is less of a concern.

In one embodiment, the beam scanning mechanism further comprises a beam chopper, and is designed to include shielding material as well. In one embodiment, the angle of the X-ray beam with respect to the normal to the front of the detector head is kept preferentially at about 10 degrees. This angle avoids the beam having to travel through the full length of an object which is commonly vertical, and provides some depth information to the screener. It should be appreciated that other ranges of energy levels may be used and other forms of radiation or energy can be used, including gamma, millimeter wave, radar or other energy sources. Any imaging system that has the potential for displaying object detail may be employed in the system and methods of the present invention.

Figure 8:
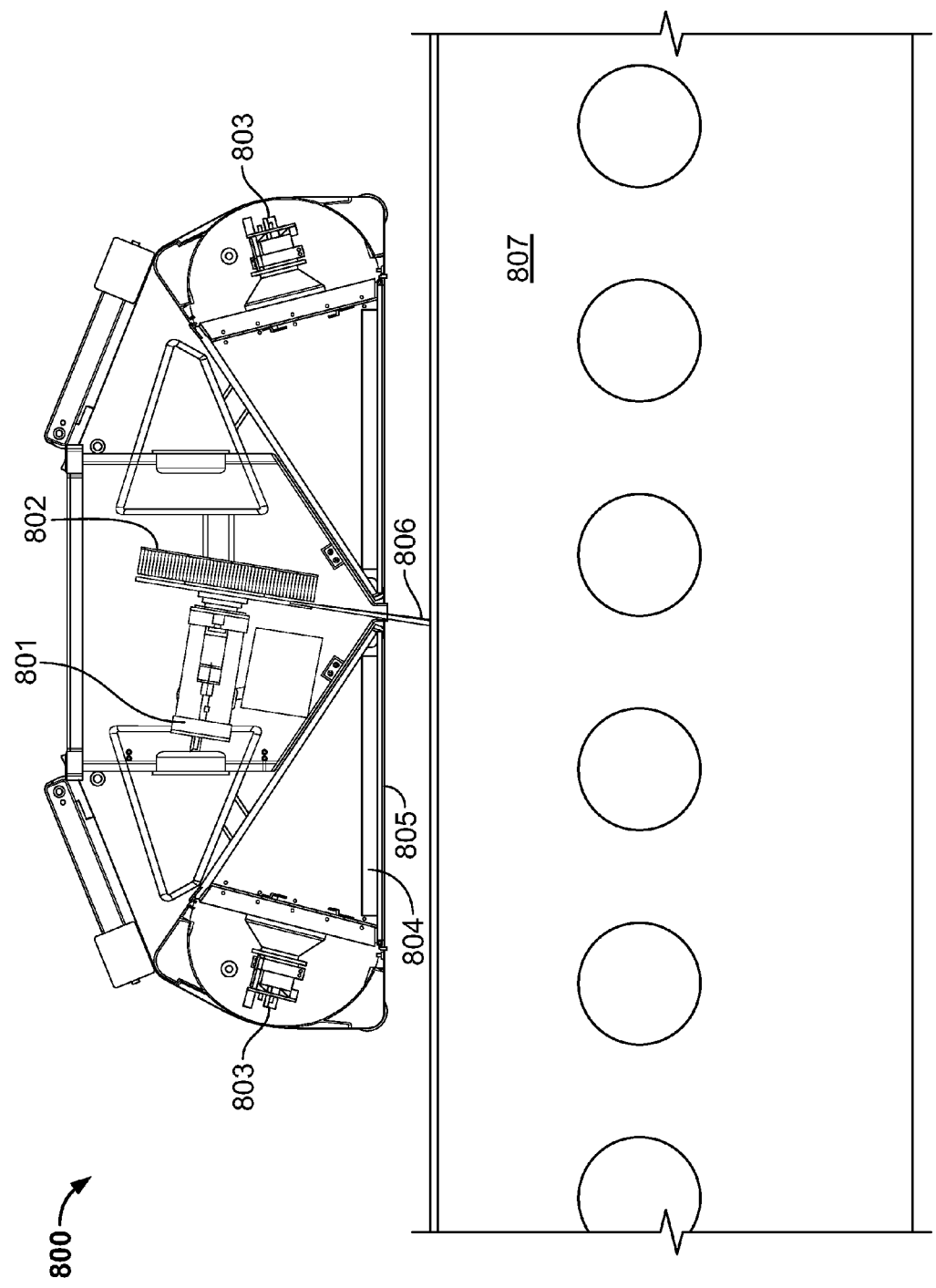
FIG. 8 is a cross-sectional view of a backscatter head of the present invention comprising a backscatter module.

FIG. 8 is a cross-sectional view of an inspection head used in one embodiment of the present invention. In one embodiment, backscatter module 800 comprises X-ray source 801, a mechanism for producing a scanning pencil beam 802, and detectors 803. A front panel 804 of backscatter module 800 employs a scintillator material 805, which detects the backscattered X-rays resultant from a pencil beam of X-rays 806 that is scanned over the surface of the object (and in this example, aircraft) 807 being inspected.

In one embodiment, detector 803 is a dual-purpose detector capable of detecting both backscatter x-rays and passive radiation. In a preferred embodiment, the x-ray and gamma-ray detectors are combined in the same module, and therefore, the same detector is employed for detecting both the backscatter x-rays and passive gamma rays. In another embodiment, the x-ray detector is different from the gamma-ray detector, especially in cases when the preferred gamma-ray detector has a response slower than few microseconds such that the detector is not appropriate for backscatter inspection.

Gamma-ray detectors and neutron detectors are also employed for passive measurements along with x-ray inspection. The passive detector consists of at least one gamma-ray detector and an optional moderated $^3$He or other neutron detectors. In one embodiment of operation, the system scans the object employing the inspection module. The object, or part of the object, is then rescanned using a passive detector.

U.S. patent application Ser. No. 12/976,861, also by the Applicant of the present invention, entitled "Composite Gamma Neutron Detection System" and filed on Dec. 22, 2010, describes a method for simultaneous detection of gamma-rays and neutrons with pulse shape discrimination to discriminate between the two effects. This method is also applicable to the current invention and is incorporated herein by reference.

As described in U.S. patent application Ser. No. 12/976,861, several nuclei have a high cross-section for detection of thermal neutrons. These nuclei include He, Gd, Cd and two particularly high cross-section nuclei: Li-6 and B-10. In each case, after the interaction of a high cross-section nucleus with a thermal neutron, the result is an energetic ion and a secondary energetic charged particle.

For example, the interaction of a neutron with a B-10 nucleus can be characterized by the following equation:

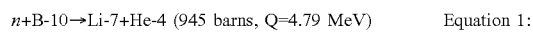

$n$+B-10→Li-7+He-4 (945 barns, Q=4.79 MeV)    Equation 1:

Here, the cross section and the Q value, which is the energy released by the reaction, are shown in parenthesis.

Similarly, the interaction of a neutron with a Li-6 nucleus is characterized by the following equation:

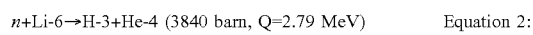

$n$+Li-6→H-3+He-4 (3840 barn, Q=2.79 MeV)    Equation 2:

It is known that charged particles and heavy ions have a short range in condensed matter, generally travelling only a few microns from the point of interaction. Therefore, there is a high rate of energy deposition around the point of interaction. In the present invention, molecules containing nuclei with a high neutron cross section are mixed with molecules that provide a scintillation response when excited by the deposition of energy. Thus, neutron interaction with Li-6 or B-10, for example, results in the emission of a flash of light when intermixed with a scintillation material. If this light is transported via a medium to a photodetector, it is then possible to convert the optical signal to an electronic signal, where that electronic signal is representative of the amount of energy deposited during the neutron interaction.

Further, materials such as Cd, Gd and other materials having a high thermal capture cross section with no emission of heavy particles produce low energy internal conversion electrons, Auger electrons, X-rays, and gamma rays ranging in energy from a few keV to several MeV emitted at substantially the same time. Therefore, a layer of these materials, either when mixed in a scintillator base or when manufactured in a scintillator, such as Gadolinium Oxysulfide (GOS) or Cadmium Tungstate (CWO) will produce light (probably less than heavier particles). GOS typically comes with two activators, resulting in slow (on the order of 1 ms) and fast (on the order of 5 μs) decays. CWO has a relatively fast decay constant. Depending on the overall energy, a significant portion of the energy will be deposited in the layer, while some of the electrons will deposit the energy in the surrounding scintillator. In addition, the copious X-rays and gamma rays produced following thermal capture will interact in the surrounding scintillator. Thus, neutron interactions will result in events with both slow and fast decay constants. In many cases, neutron signals will consist of a signal with both slow and fast components (referred to as "coincidence") due to electron interlacing in the layer and gamma rays interacting in the surrounding scintillator.

The scintillation response of the material that surrounds the Li-6 or B-10 nuclei can be tuned such that this light can be transported through a second scintillator, such as a plastic scintillator in one embodiment, with a characteristic which is selected to respond to gamma radiation only. In another embodiment, the material that surrounds the Li-6 or B-10 is not a scintillator, but a transparent non-scintillating plastic resulting in a detector that is only sensitive to neutrons.

Thus, the plastic scintillator is both neutron and gamma sensitive. When a neutron is thermalized and subsequently captured by the H in the detector, a 2.22 MeV gamma ray is also emitted and often detected. In this manner, the invention disclosed in U.S. patent application Ser. No. 12/976,861 achieves a composite gamma-neutron detector capable of detecting neutrons as well as gamma radiation with high sensitivity. Further, the composite detector also provides an excellent separation of the gamma and neutron signatures. It should be noted herein that in addition to charged particles, B-10 produces gamma rays. Therefore, in using materials that produce gamma rays following neutron capture, the result may be a detection that looks like gamma rays. Most applications, however, want to detect neutrons; thus, the disclosed detector is advantageous in that it also detects the neutrons.

Figure 9:
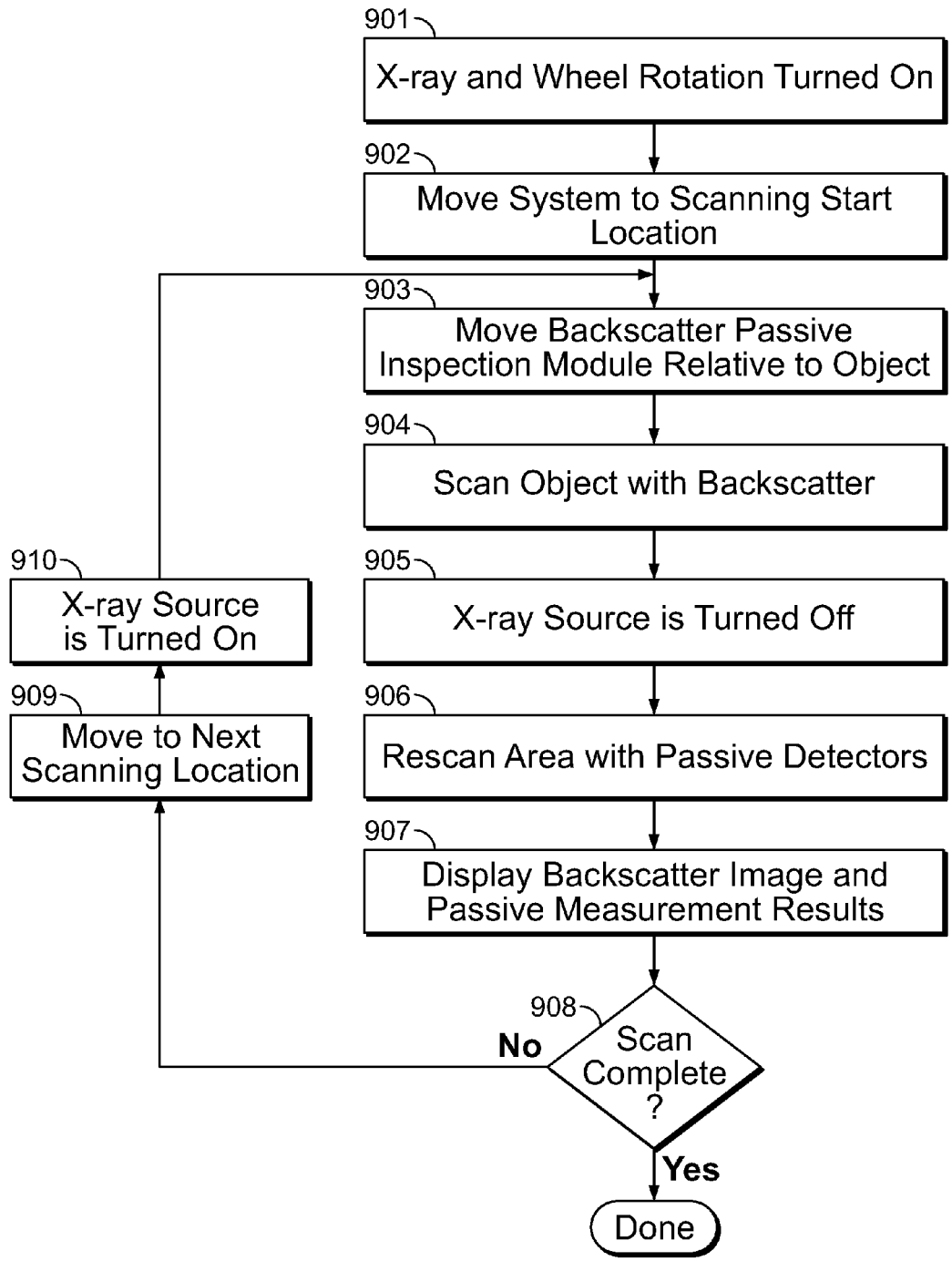
FIG. 9 is a flowchart illustrating serial X-ray backscatter and passive gamma ray detection.

FIG. 9 is a flowchart illustrating serial X-ray backscatter and passive gamma ray detection. Referring to FIG. 9, in the first step 901, the X-ray source is turned on and the beam chopping mechanism is started. In the next step 902, the system is moved to the location where scan is to be started. Thereafter, the backscatter passive inspection module is moved relative to the object for scanning, as shown in step 903. In the next step 904, the object is scanned and backscatter data is received. The X-ray source is then turned off, as shown in step 905. The area is then rescanned with passive detectors, as shown in step 906. After this, image generated from backscatter data and passive measurement results are displayed, as shown in step 907. The system then checks if the scan is complete, as shown in step 908. In cases where the scan is not complete, the system moves to the next scanning location, as shown in step 909. The X-ray source is then turned back on, as shown in step 910, and the scan process is repeated until complete.

In another embodiment, the backscatter and passive detector works in an interleaved mode, in such a way that there is no need to rescan the object. In this mode, the backscatter measurement is performed when the beam of radiation impinges on the object.

During the time the pencil-beam impinges unto the object, the X-ray system (via the inspection head) collects data to produce images. When the pencil beam is blocked and there is no radiation beam exiting from the beam chopping mechanism, the passive detectors are enabled to collect gamma-rays and neutrons. The main advantage of simultaneous inspection is the reduced logistic complexity and shorter scan time compared with performing X-ray and passive detection separately.

Figure 10:
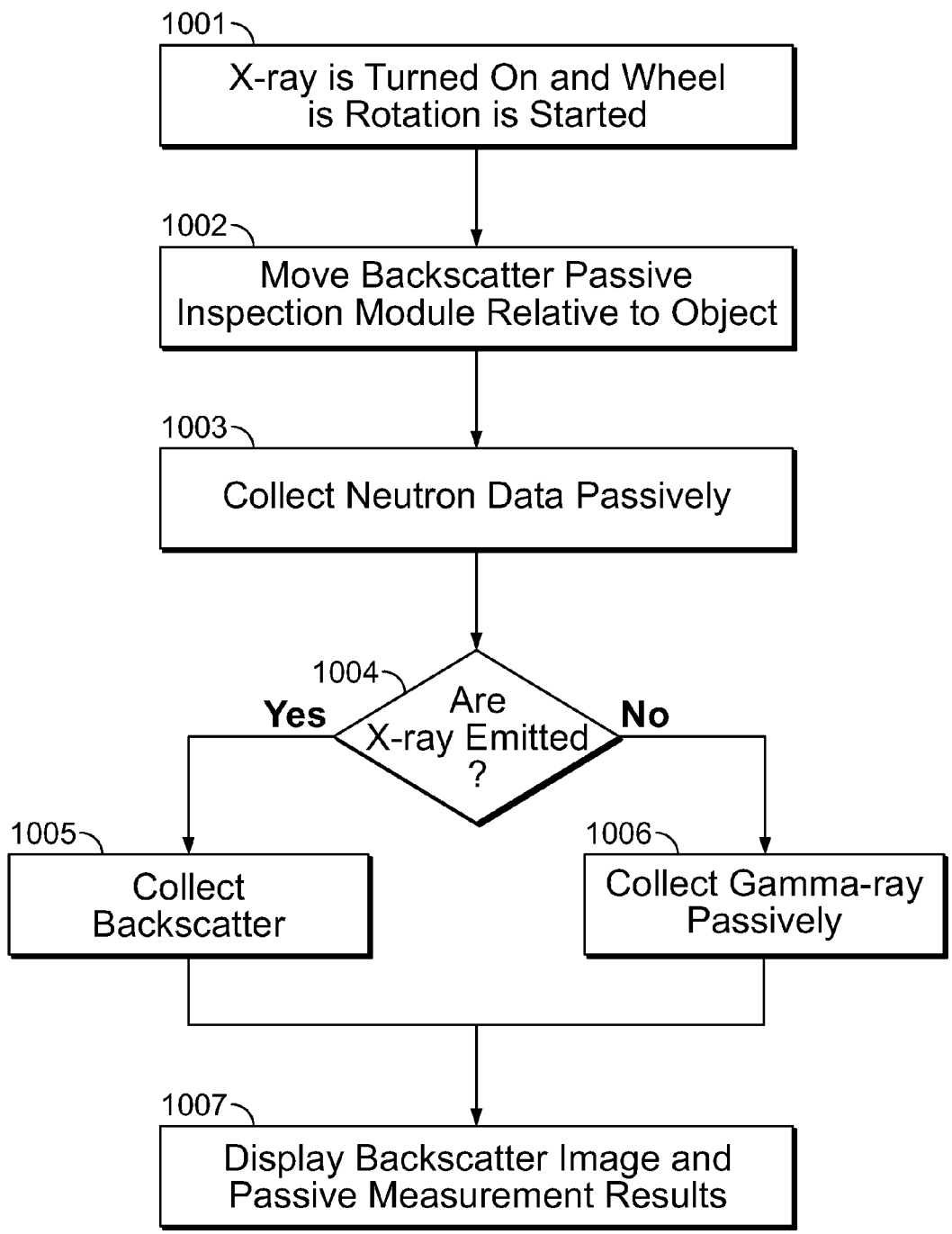
FIG. 10 is a flowchart illustrating interleaved X-ray backscatter and passive gamma ray detection.

FIG. 10 is a flowchart illustrating interleaved X-ray backscatter and passive gamma ray detection. Referring to FIG. 10, in the first step 1001, X-ray is turned on and the beam chopping mechanism is started. The beam chopping mechanism comprises, in one embodiment, a spinning wheel that can be rotated to periodically block the beam. In the next step 1002, the backscatter passive inspection module is moved relative to the object for scanning Next, neutron data is collected passively, as shown in step 1003. Thereafter, the system checks if X-rays are being emitted, in step 1004. Thus, if X-ray beam is being emitted, and is not blocked, the system collects backscatter data, as shown in step 1005. However, if the beam chopping mechanism is currently blocking the X-ray beam, the system collects data pertaining to passive gamma rays emitted from the object. This is shown in step 1006. In the end, image generated from backscatter data and passive measurement results are displayed, as shown in step 1007.

The results of the passive detection measurements and the X-ray images are data fused to improve detection of nuclear and radioactive materials. For example, dark areas in the backscatter image may indicate the presence of partially shielded nuclear or radioactive materials. If higher levels of radiation occur in these dark areas, there is a stronger indication of the presence of these threat materials.

In one embodiment, a spinning wheel having a plurality of pinholes therein is employed to produce a pencil beam of radiation through at least one pinhole, during which time backscatter radiation detection is active. In one embodiment, the spinning wheel effectively "blocks" the x-ray fan beam (and resultant pencil beam) from exiting, due to the position of the pinholes in the spinning wheel, during which time passive radiation detection is active. Thus, passive radiation measurement proceeds when the beam is "off" or blocked by the spinning wheel geometry, where there is no pinhole for the radiation to exit.

FIG. 11 is an illustration of an embodiment of a spinning wheel as used in the system of the present invention, showing the pencil beam in an "on" position, wherein a backscatter measurement is taken. As shown in FIG. 11, spinning wheel 1100 comprises a disc fabricated from shielding material defining at least one pinhole 1105 through which a fan beam 1110 "exits" through the spinning wheel as pencil beam 1115. In one embodiment, spinning wheel 1100 comprises two pinholes 1105. The pencil beam radiation, and thus backscatter measurement capability, is "on" when the fan beam 1110 exits the spinning wheel as a pencil beam 1115.

FIG. 12 is an illustration of one embodiment of a spinning wheel as used in the system of the present invention, showing the pencil beam in an "off" position, wherein a passive measurement is taken. As shown in FIG. 12, as spinning wheel 1200 is rotated, there are times when the fan beam 1210 does not coincide with at least one slit 1205. During this time, the fan beam 1210 is shielded by the spinning wheel 1200, and therefore, no radiation exits the system. It is during these times when the fan beam 1210 is "off" that a passive radiation measurement is taken.

It should be noted herein that employing a spinning wheel having two pinholes is only exemplary and that the basic approach can use any number of pinholes in the spinning wheel geometry as long as a passive measurement is performed when the pencil beam is off.

In another embodiment, a beam chopping mechanism is employed, wherein the beam chopping mechanism is designed to present a helical profile shutter (aperture), formed on a cylinder, for X-ray beam scanners. In one embodiment, a radiation shield is provided on a radiation source such that only a fan beam of radiation is produced from the source whereby the fan beam of radiation emits X-rays which then pass through the spin-roll chopper, which acts as an active shutter. Thus, when the spin-roll chopper and therefore, helical aperture(s) is rotating, there is only a small opening for the X-ray fan beam to pass through, which provides the moving flying spot beam. In this embodiment, the slits are configured in such a way that there is at least one gap where no pencil beam is produced. U.S. patent application Ser. No. 13/047,657, entitled "Beam Forming Apparatus" and assigned to the Applicant of the present invention, is herein incorporated by reference in its entirety.

Figure 13A:
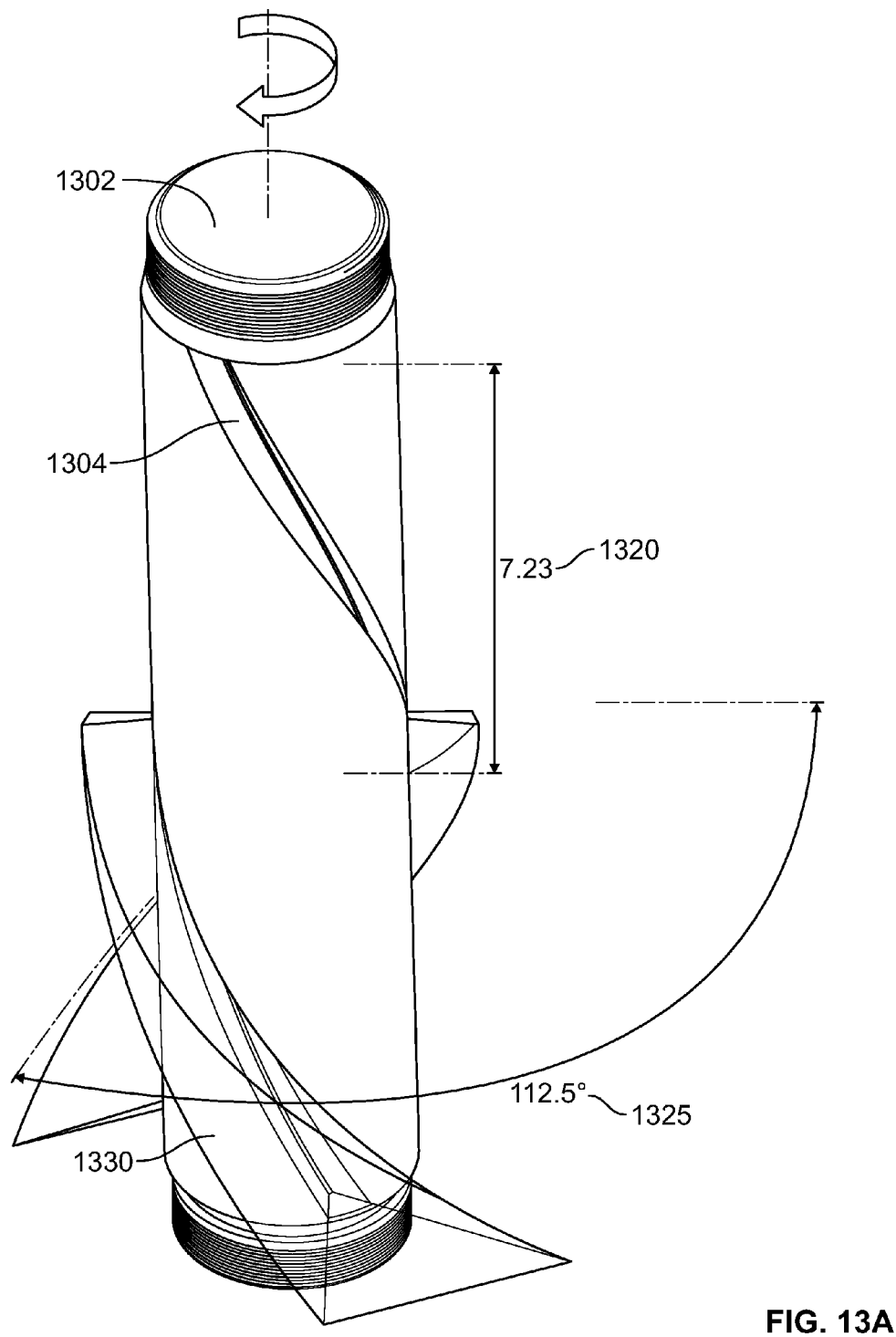
FIG. 13A is a mechanical illustration of an exemplary design of one embodiment of a spin-roll chopper as used in the present invention.

FIG. 13A illustrates an exemplary design for one embodiment of the spin-roll chopper, as used in various embodiments of the present invention. Beam chopper 1302 is, in one embodiment, fabricated in the form of a hollow cylinder having helical slits 1304 for "chopping" the X-ray fan beam. The cylindrical shape enables the beam chopper 1302 to rotate about the Z-axis and along with the helical apertures 1304, create a spin-roll motion, which provides effective scanning and therefore good image resolution, as described below, while at the same time keeping the chopper lightweight and having less moment of inertia as the spin-roll mass is proximate to the axis of rotation. Stated differently, the radius of the spin-roll chopper is small compared to spinning wheel or disc beam chopping mechanisms, and is advantageous in some cases.

It should be noted that the helical twist angle 1325 represents the angle of motion of the helical aperture from the y-axis (center line) when the cylinder is spun about the z-axis a total of 90 degrees.

Thus, an X-ray beam scanner employing the spin-roll chopper as in one embodiment of the present invention effectuates beam chopping by rotating the hollow cylinder 1302 machined with at least two helical slits 1304, enabling X-ray beam scanning with both constant and variable linear scan beam velocity and scan beam spot size. The spin-roll chopper enables both constant and variable linear scan beam velocity by manipulating the geometry of the helical apertures. In one embodiment, the velocity is varied or kept constant by manipulating the pitch and roll of the helical apertures along the length of the spin-roll chopper. Thus, it is possible to have a constant speed or to slow the scan down towards areas where more resolution is desired.

The spin-roll chopper as described with respect to the present invention also enables variable and constant beam spot size by manipulating the geometry of the helical apertures, thus varying the resultant beam power. In one embodiment, the actual width of the aperture is manipulated to alter the beam spot size. In one embodiment, the width of the helical aperture varies along the length of the spin-roll chopper cylinder to compensate for the varying distance of the aperture from the center of the source and allow for uniform beam spot projection along the scan line. Thus, in one embodiment, the farther the aperture is away from the source, the narrower the width of the helical aperture to create a smaller beam spot size. In one embodiment, closer the aperture is to the source, wider the helical aperture to create a larger beam spot size.

Helical slits 1304 are fabricated to ensure that the projection of the X-ray beam is not limited by dual collimation of the two slits. Dual collimation refers to the concept whereby the X-ray beam will pass through two helical slits at any given point in time. The resultant X-ray beam trajectory 1330 is also shown in FIG. 13A. In one embodiment, a pair of helices will produce one travelling beam. In another embodiment, additional pairs of helices may optionally be added to produce additional travelling or flying spot beams depending upon scanning requirements.

Figure 13B:
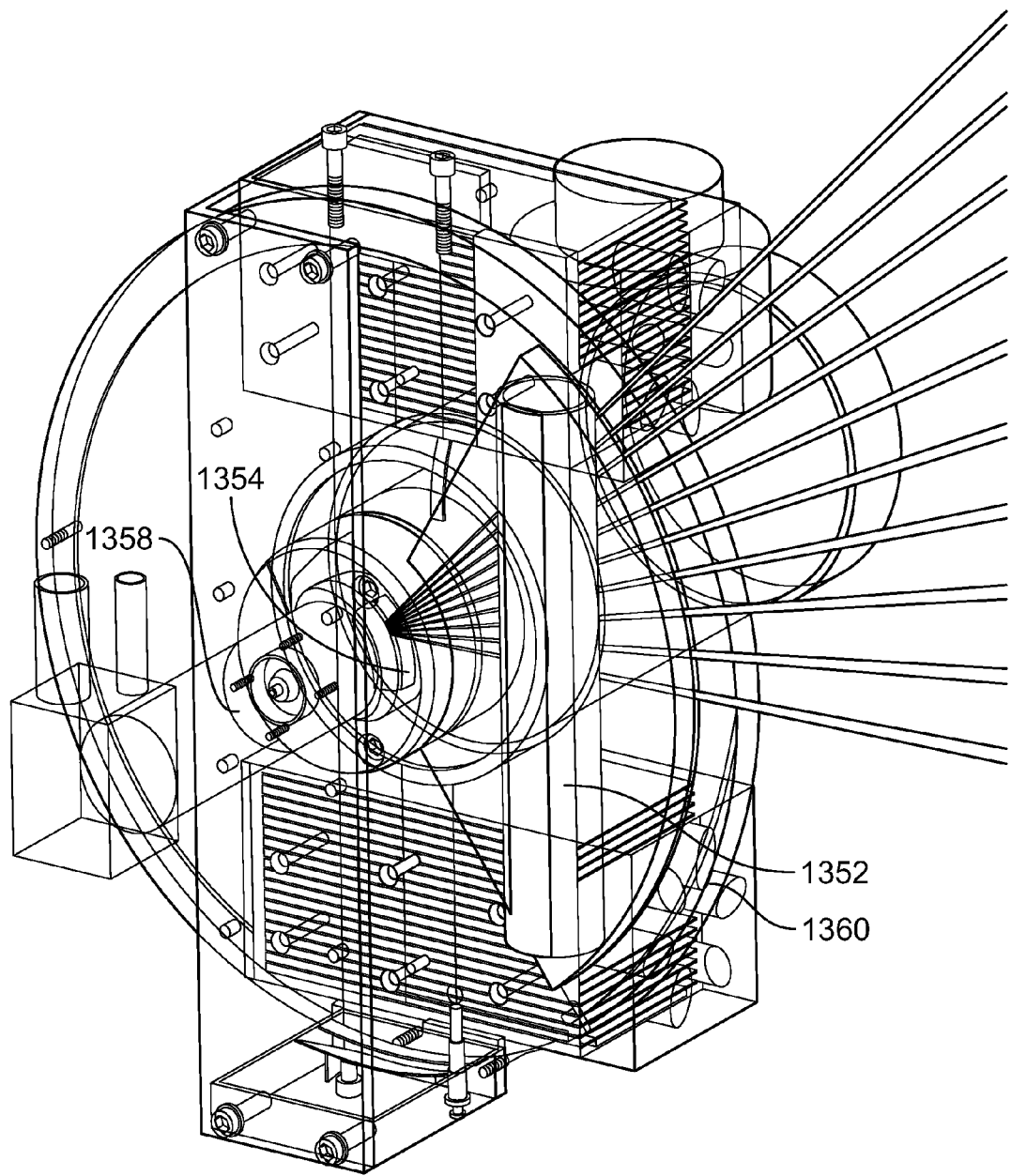
FIG. 13B illustrates the spin-roll chopper mechanism employed in one embodiment of the present invention with an X-ray source.

In an embodiment of the present invention a plurality of viewing angles ranging from sixty degrees to ninety degrees can be obtained through the helical slits in the spin-roll chopper. FIG. 13B illustrates a beam chopping mechanism using the spin-roll chopper described with respect to FIG. 13A. Referring to FIG. 13B, the cylindrical spin-roll chopper 1352 is placed in front of a radiation source 1354, which, in one embodiment, comprises an X-ray tube. In one embodiment, rotation of the chopper 1352 is facilitated by including a suitable motor 1358, such as an electromagnetic motor. The speed or RPM of rotation of the spin-roll chopper system is dynamically controlled to optimize the scan velocity. In one embodiment, the spin-roll chopper system is capable of achieving speeds up to 80K RPM.

In yet another embodiment, a scanning pencil beam is generated by any one of the approaches described above or any other approach as is known to those of ordinary skill in the art and deactivated by turning off the X-ray source (in contrast with previous embodiments, where the source is "blocked" by use of the spinning wheel or spin-roll chopper). Examples of suitable x-ray sources include, but are not limited to gridded sources, field emission electron sources (e.g. carbon nanotubes) or any other source that can switch the beam on-off within a few microseconds. However, it should be noted that if the wheel or spin-roll chopper is spinning slower, then the time between switching the X-ray source on and off can be longer. Therefore, it can be stated that the time it takes for the X-ray source to be switched on and off is relative to the rotational frequency of the spinning wheel, on the order of a fraction of the rotational time of the source, which is in the range of less than 1%. By way of example, if the rotational frequency if 2400 rpm (rotations per minute) and there are four pinholes, the time would be 6.25 ms ON and 6.25 ms OFF. If the spinning wheel is rotating at 240 rpm, then the times would be 62.5 ms ON and 62.5 ms OFF. Thus, the expression for the preferred time is as follows:

$$\text{Time [ms]} = ((60/\text{frequency [rpm]})/\text{number of pinholes}) \times 1000 \qquad \text{Equation 3:}$$

Figure 14:
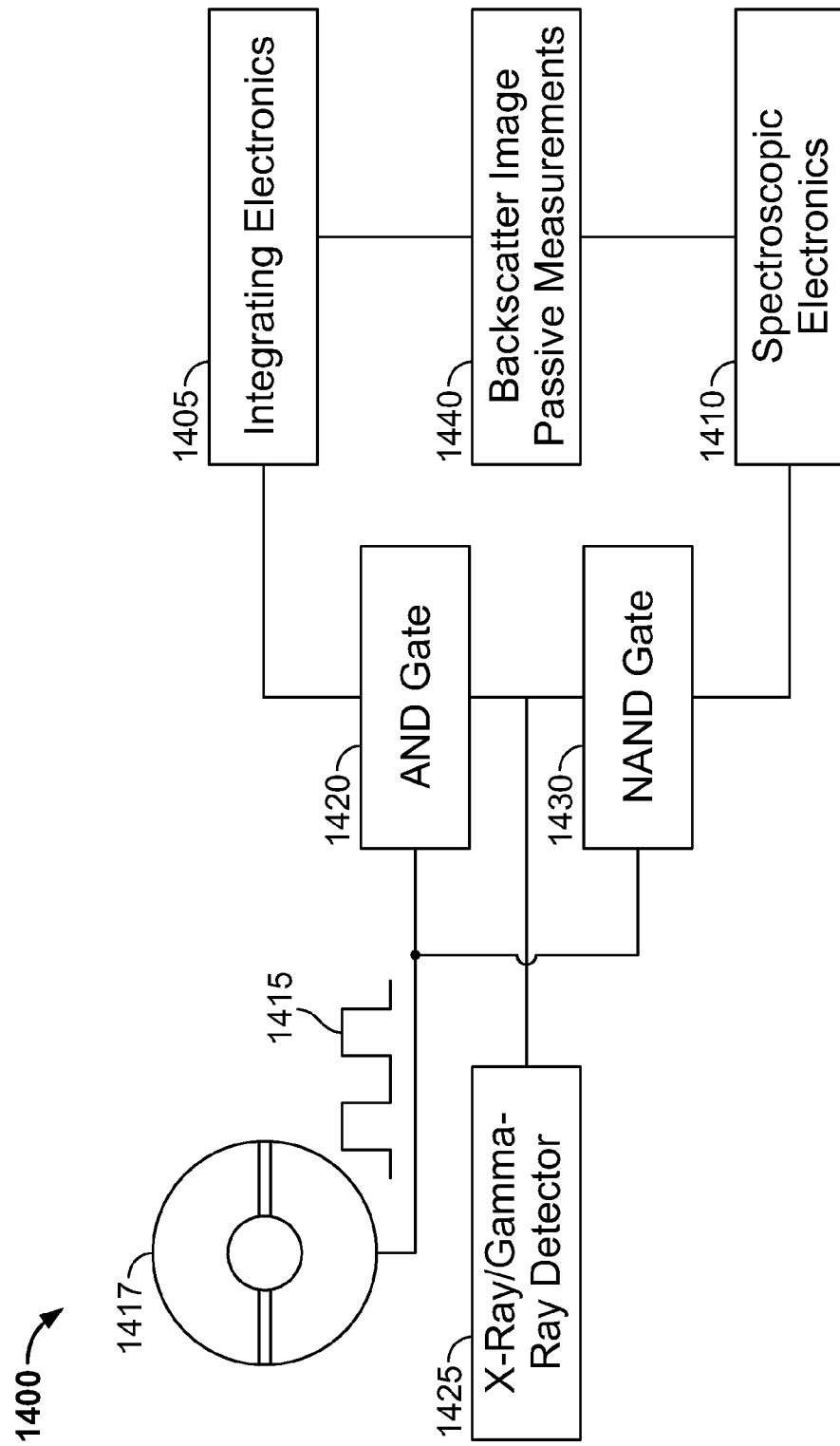
FIG. 14 is a block diagram showing signal processing with two different sets of electronics when the backscatter x-ray detector and passive gamma ray detector are the same.

FIG. 14 is a block diagram 1400 showing signal processing with two different sets of electronics when the backscatter x-ray detector and passive gamma-ray detector are the same. That is, the detector is dual-purpose, capable of detecting both backscattered X-rays and passive radiation. The backscatter system uses integrating electronics 1405, while the passive detector uses spectroscopic electronics

1410. Both set of electronics 1405, 1410 are gated with a gating signal 1415 from the spinning wheel control 1417. This produces a high signal when the system emits a pencil beam of radiation.

The backscatter integrating electronics 1405 employs an AND gate 1420 to measure backscatter radiation only when the beam is on, as described above with respect to FIG. 3A. The passive detector 1425 uses a NAND gate 1430 to measure only gamma rays when the x-ray pencil beam is off, as described above with respect to FIG. 13B. The optional neutron detector (not shown) need not be gated and can measure neutrons at all times.

The resultant backscatter image and results of the passive gamma-ray and neutron measurements are then shown on the screen (separately or combined).

The inspection system refers to any backscatter and passive radiation detection system that can be deployed in a scanning vehicle, portal, gantry, trailer, mobile platform or other scanning configurations. The system is also designed such that it can be moved relative to the object or such that the object can be moved relative to the system.

Reference will now be made to a specific embodiment of an aircraft inspection system that employs the active and passive radiation techniques as described in the present specification. It should be noted herein that such embodiment is exemplary only and that any system can be designed such that it takes advantage of the methods described above.

U.S. patent application Ser. No. 12/916,371, entitled "Mobile Aircraft Inspection System" and filed on Oct. 29, 2010, is herein incorporated by reference in its entirety.

Figure 15:
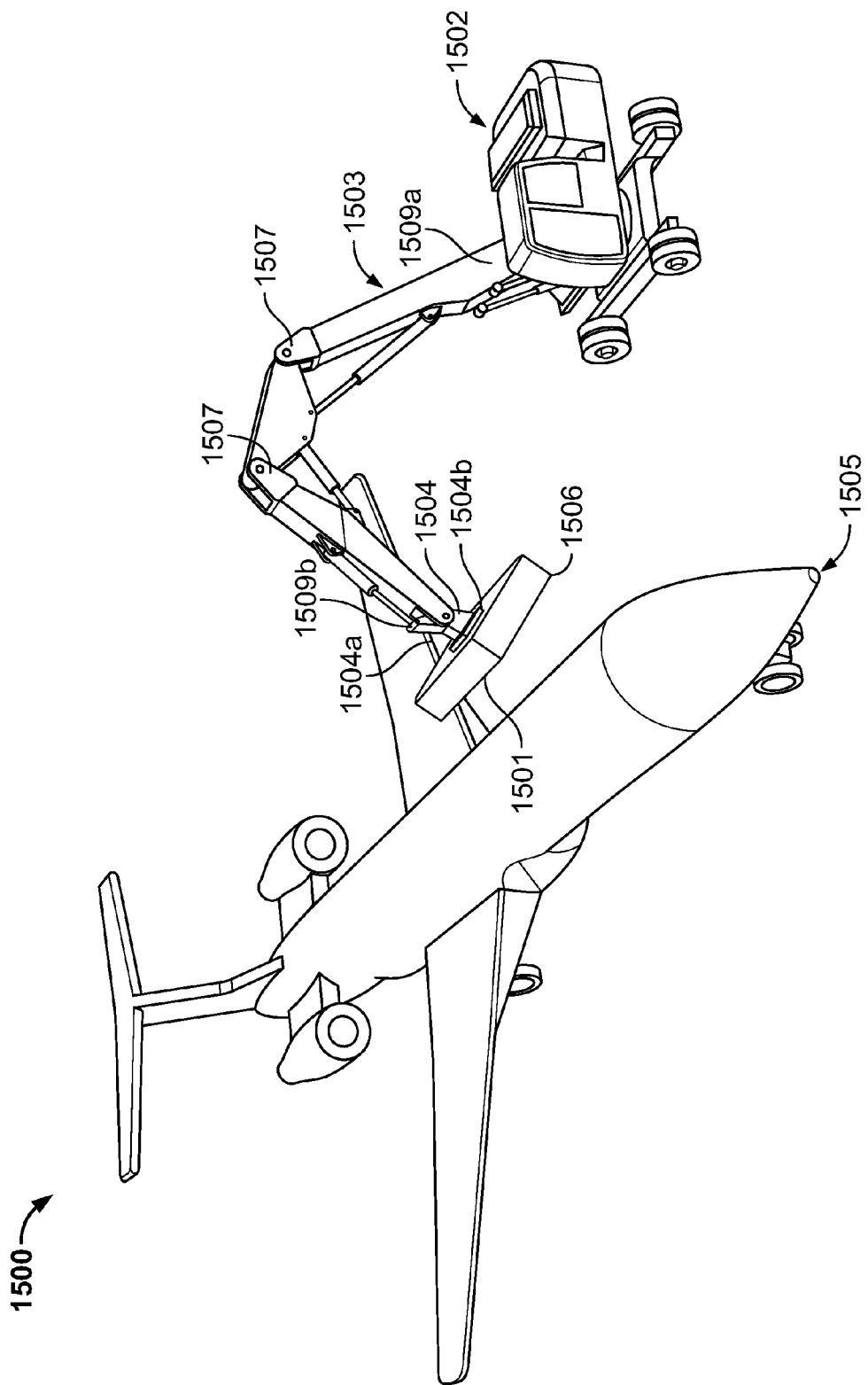
FIG. 15 illustrates the basic functional design of the backscatter-based aircraft inspection system of the present invention.

FIG. 15 illustrates the overall system design of one embodiment of the present invention. Referring to FIG. 15, aircraft inspection system 1500, in one embodiment, comprises inspection head 1501, vehicle or transport cart 1502, and manipulator arm 1503. In one embodiment, inspection head 1501 comprises an inspection module, further comprising an X-ray source, a beam scanning mechanism and X-ray detectors. The inspection module is described in greater detail above with respect to FIG. 8. In one embodiment, vehicle or transport cart 1502 is any standard vehicle suitable for movement about an aircraft 1505.

In one embodiment, vehicle 1502 is movably connected to first, proximal end 1609*a* of manipulator arm 1503 and inspection head 1501 is movably connected to second, distal end 1509*b* of manipulator arm 1503 via a customized attachment 1504. Manipulator arm 1503 is described in greater detail below. In one embodiment, customized attachment 1504 is designed for use with the system of the present invention. In another embodiment, customized attachment 1504 may be available as an off-shelf component, as long as it achieves the objectives of the present invention, as described below.

In one embodiment, the inspection head 1501 is mounted on manipulator arm 1503 in such a manner that it allows for scanning of a variety of aircraft sizes, shapes and configurations. The manipulator arm 1503 is also capable of rotating and moving the inspection head 1501 in all directions. In one embodiment, customized attachment 1504 is movably attached to manipulator arm 1503 at a first joint 1504*a* and movably attached to inspection head 1501 at a second joint 1504*b*. Thus customized attachment 1504 allows for the inspection head 1501 to be moved and rotated about first joint 1504*a* and second joint 1504*b*. In one embodiment, first joint 1504*a* and/or second joint 1504*b* is a ball and socket type joint that allows for at least one movement, such as but not limited to tilt, swivel and/or rotation at the joint, and in one embodiment, full motion. The ability to move and rotate the source at both the first attachment joint 1504*a* and at the second attachment joint 1504*b* allow for the system to follow the contour of the aircraft and thus, adjust to its shape using several degrees of movement freedom.

In addition, manipulator arm 1503 has multiple articulation or pivot joints 1507 that allow for complex motions.

In one embodiment, in order to avoid damage to the aircraft 1505 being inspected, the inspection head 1501 includes at least one proximity sensor 1506. In one embodiment, the sensors are redundant, so if one fails to operate, another sensor will still alert when the system is too close to the aircraft. The at least one proximity sensor 1506 is configured to avoid collision and keep the inspection head 1501 at a safe distance from the aircraft 1505. Therefore, once the at least one proximity sensor 1506 is triggered, the inspection system 1500 will cease operation. When inspection system 1500 ceases operation, the scanning head is refracted and the system cannot be operated until the sensor alarm is cleared.

In one embodiment, the at least one proximity sensor 1506 is connected and controlled via hardware.

In one embodiment, manipulator arm 1503 includes at least one proximity sensor. In one embodiment, vehicle 1502 also includes at least one proximity sensor.

To select appropriate design specifications for the vehicle and the manipulator arm, the critical areas of focus are: a) the distance from the source/detector to the aircraft, b) the controlled motion of the source/detector, and c) collision avoidance for both the vehicle and the manipulator with the aircraft. In one embodiment, an optimal distance from the source/detector arrangement to the aircraft rages from ½ meter up to two meters. In one embodiment, the distance is chosen to provide optimal image resolution, inspection coverage and signal strength. The weight of the source/detector in conjunction with the maximum height and maximum reach that the manipulator arm must obtain further determines the dimensions of the vehicle platform. It should be understood by those of ordinary skill in the art that the weight of the source is largely dependent on source type, and that source type is chosen based on the object under inspection and scanning requirements. Scanning sequence, motion speed, and tolerances for position and vibration also direct the specifications for the manipulator arm and/or any special attachments or tooling. As mentioned earlier, in order to minimize development time and costs in one embodiment, any suitable off-the-shelf vehicle and/or manipulator arm may be employed and modified as per the design requirements of the present invention. In one embodiment, the height and reach of the manipulator arm and weight and/or dimensions of the inspection head are a function of the size of the airplane or large cargo containing entity being scanned.

Figure 16:
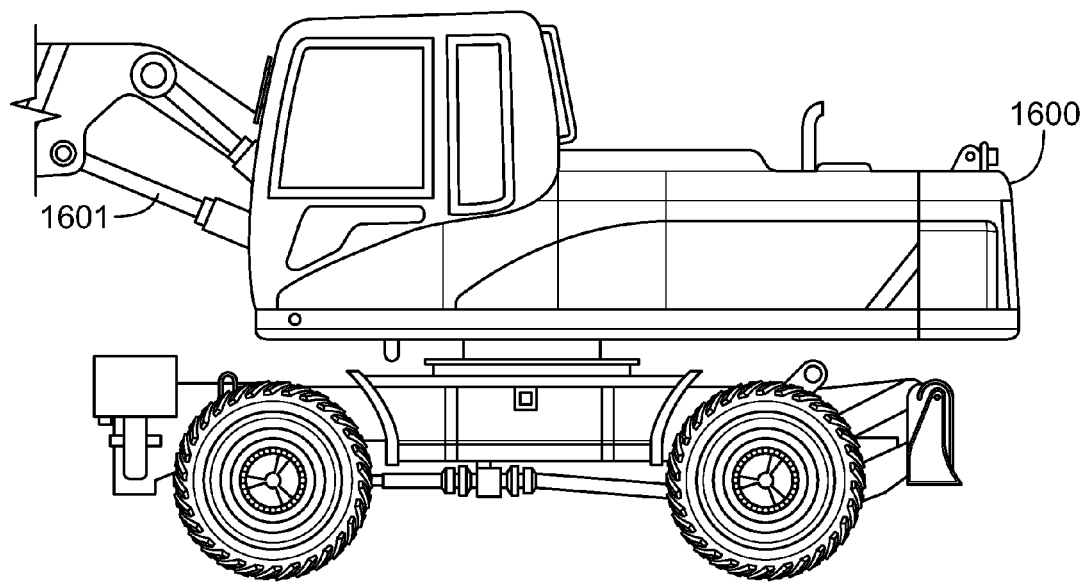
FIG. 16 illustrates an exemplary vehicle that can be used with the mobile aircraft inspection system of the present invention.

FIG. 16 illustrates an exemplary vehicle 1600 that is connected to a backscatter module (not shown), via manipulator arm 1601, for the aircraft inspection system of the present invention. In one embodiment, for example, the vehicle 1600 may be a wheeled excavator or a similar vehicle.

Figure 17:
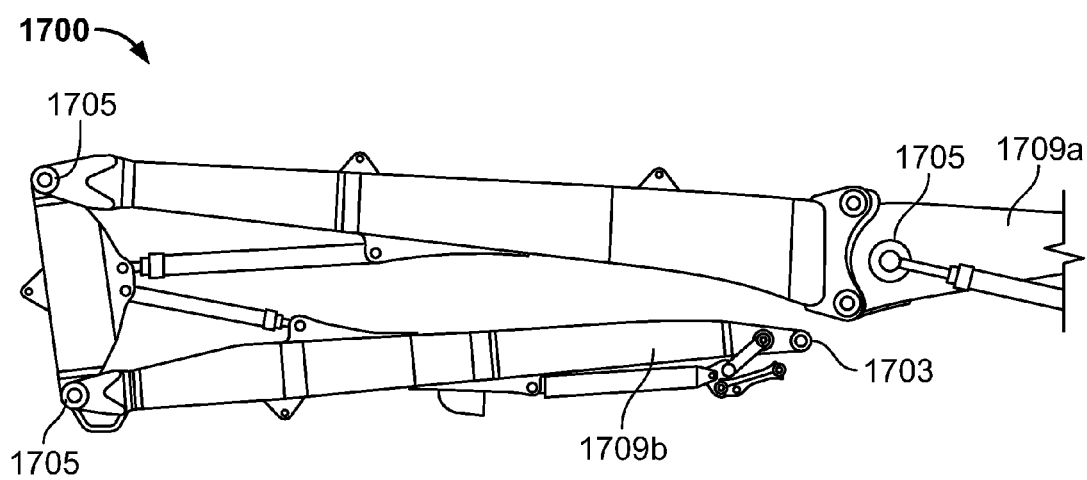
FIG. 17 illustrates an exemplary manipulator arm used for mounting the inspection head or radiation source of the system of present invention.

FIG. 17 illustrates an exemplary manipulator arm 1700 that is used for mounting a backscatter module (not shown) for the aircraft inspection system of the present invention. In one embodiment, the manipulator arm 1700 comprises a multi-purpose hydraulic boom. The boom design allows for the flexibility of attaching the vehicle (not shown) to a first, proximal end 1709*a* while attaching standard or custom tools at its second, distal end 1709*b*. Second, distal end

1709*b*, in one embodiment, is modified to allow for attachment of a backscatter inspection module at joint 1703.

In one embodiment, manipulator arm 1700 is operated using computer-controlled motion and has at least five degrees of freedom for positioning in all directions, including up-down, left-right, in/out and rotation. In one embodiment, the system further comprises a controller unit, which can be remote from the system or located within the vehicle, for communicating motion instructions to controllers located in the scanning head or gantry unit which, in turn, directs motors to move the scanning head and/or gantry unit in the requisite direction. One method of controlling motion of the vehicle and the manipulator arm using a computer involves referring to a database of airplane models, stored in a memory on the computing system. Each entry in the database corresponds to a plane contour. This database enables the motion-control program to generate a scan plan, which is used to control the motion of the arm and the head to scan the airplane according to the plan. Further, for some planes, it may not be possible to scan the entire plane from one vehicle position. Therefore, the motion control program analyzes the various positions required and the system scans the plane accordingly.

In one embodiment, the arm is capable of full 360 degree rotation. The manipulator 1700 is linearly extensible and contractible, and the extension and contraction can be achieved with a complex motion of the various parts of the manipulator arm. The system scans the aircraft by moving the arm at a nearly constant distance from the surface of the aircraft.

The manipulator arm 1700 is also equipped with the capability of source rotation at the joint 1703, as described above. The ability to rotate and move the source through several degrees of freedom at attachment joint 1703, allow for the system to follow the contour of the aircraft and thus, adjust to its shape. The manipulator arm of the present invention has multiple articulation or pivot points 1705 that allow for complex motions, including but not limited to extension and contraction.

In one embodiment, the aircraft inspection system of the present invention is capable of producing high-resolution images that enable the operator to easily identify concealed threat and contraband items. In one embodiment, a database or threat library containing standard images of airplanes is employed to compare resultant scans of the aircraft under inspection with images collected from planes of the same model to determine anomalies.

In one embodiment, depending on the size of the airplane, the images of parts of the planes are collected separately. These images can then be displayed separately, or they could be "stitched" together show a combined image.

The aircraft inspection system of the present invention is capable of accurately detecting both organic materials, such as solid and liquid explosives, narcotics, ceramic weapons, as well as inorganic materials, such as metal. In one embodiment, the aircraft imaging system uses automated threat software to alert an operator to the presence of potential inorganic and organic threat items. In one embodiment, the system is capable of transmitting backscatter and photographic images to an operator or remote inspector wirelessly.

The aircraft inspection system of the present invention is designed to be modular to enhance transportability and ease of assembly. In one embodiment, the individual modules— the vehicle, the manipulator arm, the scanning head, and optionally detector cart can be assembled on site and/or customized per application. In addition, in another embodiment, the system is ready to deploy and requires no assembly.

The system is also designed to be rugged so that it can withstand harsh environments for outdoor deployments even in inclement conditions. In one embodiment, the power required to run the system is provided on-board allowing the system to operate anywhere on the airfield. In one embodiment, the aircraft inspection system of the present invention is scalable for inspecting any aircraft size from executive jets to Airbus 380. Thus, the size of the vehicle and arm can be scaled to the size of the aircraft.

Figure 18:
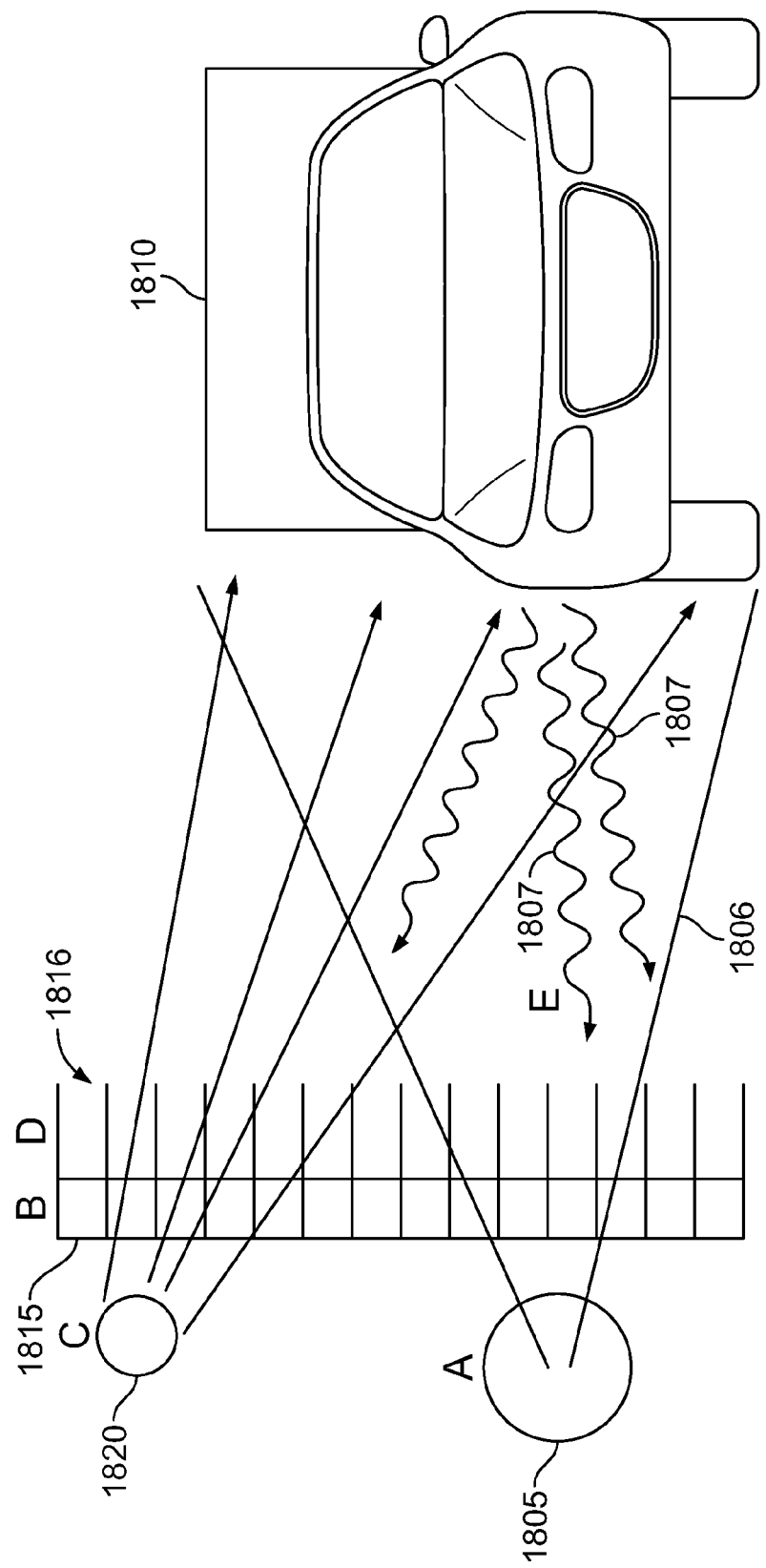
FIG. 18 is an illustration of another embodiment of the covert mobile inspection vehicle, shown in FIG. 1A, further illustrating an on-board X-ray scanning system.

FIG. 18 shows another embodiment of the X-ray scanning system 1800 of the present invention that additionally uses a multi-element scatter collimator 1816 to allow use of fan-beam X-ray irradiation to generate the backscatter image. Here, the X-ray source 1805 emits a fan beam 1806 of radiation towards the object 1810. A segmented detector array 1815 is located behind a multi-element collimator 1816, one detector element per collimator section. The collimator 1816 is designed to permit X-rays to enter from a narrow angular range, typically less than +/−2 degrees to the perpendicular to the detector array 1815. X-rays 1807 scattering from various points in the object 810 which lie within the acceptance angle of, for example, the collimator element 1816 are detected and associated to the appropriate corresponding part of the generated radiographic X-ray image. Again, a sensor 1820 is provided to measure distance to the surface of the object 1810 in order to correct the X-ray backscatter signal and produce a quantitative image scaled by effective atomic number. U.S. patent application Ser. No. 12/993,831, also by Applicant of the present invention, entitled "High-Energy X-Ray Inspection System Using A Fan-Shaped Beam and Collimated Backscatter Detectors", and filed on Nov. 19, 2010, discloses use of such a multi-element scatter collimator and is hereby incorporated by reference in its entirety.

Figure 19:
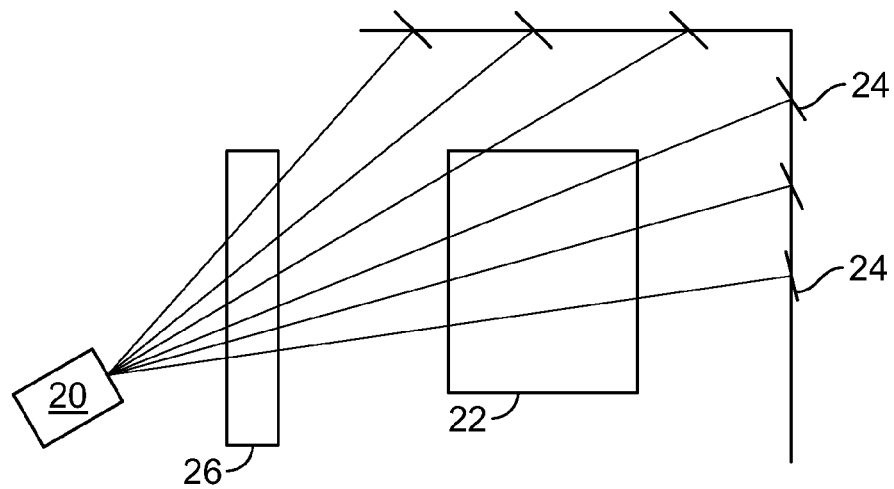
FIG. 19 is a schematic representation of components of a scanning system that may be employed in accordance with the present invention.
Figure 20:
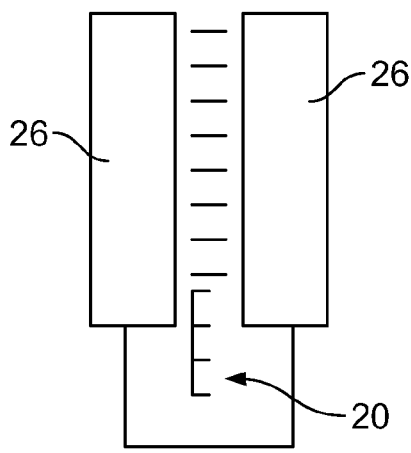
FIG. 20 is a schematic representation of components of a scanning system that may be employed in accordance with the present invention.

A system configuration according to an embodiment of the invention disclosed in U.S. patent application Ser. No. 12/993,831 is outlined in FIGS. 19 to 21. Here, an X-ray linear accelerator 20 is used to fire a collimated fan-beam of high energy (at least 900 keV) X-radiation through an object 22 under inspection and to a set of X-ray detectors 24 which can be used to form a high resolution transmission X-ray imaging of the item under inspection. The X-ray linear accelerator beam is pulsed, so that as the object under inspection moves through the beam, the set of one-dimensional projections can be acquired and subsequently stacked together to form a two-dimensional image.

In this embodiment, an X-ray backscatter detector 26 is placed close to the edge of the inspection region on the same side as the X-ray linear accelerator 20 but offset to one side of the X-ray beam so that it does not attenuate the transmission X-ray beam itself. As shown in FIG. 10, it is advantageous to use two backscatter imaging detectors 26, one on either side of the primary beam. In some embodiments the backscatter detectors may be arranged differently. In some embodiments there may be only one backscatter detector. In other embodiments there may be more than two such detectors.

In contrast to known backscatter imaging detectors which use the localisation of the incident X-ray beam to define the scattering region, the backscatter imaging detector described, is able to spatially correlate the intensity of backscattered X-ray signals with their point of origin regardless of the extended fan-beam shape of the X-ray beam.

Figure 21:
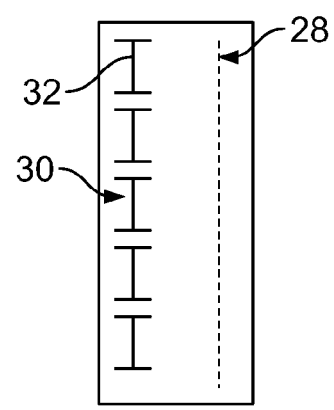
FIG. 21 is a schematic representation of components of a scanning system that may be employed in accordance with the present invention.

In the backscatter imaging detector 26, this spatial mapping is performed using a segmented collimator 28 in zone plate configuration as shown schematically in FIG. 21. Normally, a zone plate will comprise a series of sharply defined patterns whose impulse response function is well known in the plane of a two-dimensional imaging sensor that is located behind the sensor. In the present case, the energy of the X-ray beam to be detected is typically in the range 10 keV to 250 keV and so the edges of the zone plate pattern will not be sharp. For example, a zone plate fabricated using lead will require material of thickness typically 2 mm to 5 mm. Further, it is expensive to fabricate a high resolution two-dimensional imaging sensor of the size that is required in this application.

Figure 22:
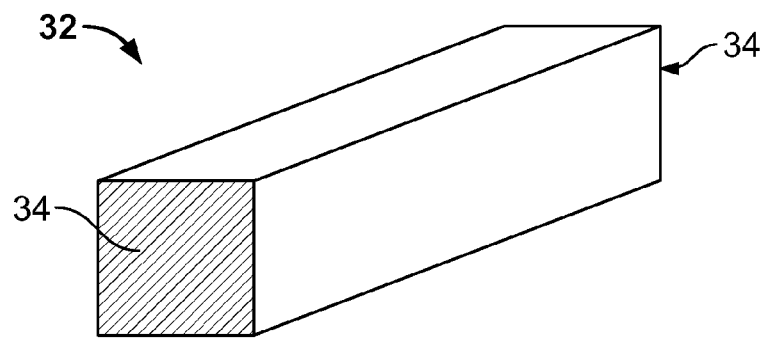
FIG. 22 shows a schematic view of a detector element that may be employed in accordance with the present invention.

However, it is noted that the radiation beam is well collimated in one direction (the width of the radiation fan beam) and therefore the imaging problem is reduced to a one-dimensional rather than a two-dimensional problem. Therefore a backscatter detector in the form of an effectively one dimensional imaging sensor 30 is provided behind the zone plate 28. To address this problem an elemental backscatter detector is used in this embodiment. As shown in FIG. 21, the detector 30 comprises a plurality of detector elements 32. FIG. 22 illustrates a detector element 32 suitable for use in this example. Here, the detector element 32 comprises a bar of scintillation material (about 100 mm long in this example) and is supplied with a photo-detector 34 at either end. The photo-detector 34 may advantageously be a semiconductor photodiode or a photomultiplier tube. X-ray photons that interact in the scintillation material emit light photons and these will travel to the two photo-detectors where they may be detected. It may be shown that the intensity of the light reaching each photo-detector is in proportion to the distance of the point of interaction from the face of the photo-detector. Therefore, by measuring the relative intensity at the two photo detectors, the point of interaction of the X-ray photon with the detector can be resolved.

Referring back to FIG. 1A, the covert surveillance vehicle 105 is equipped with a plurality of other sensors 110, apart from the X-ray scanning system, in accordance with an aspect of the present invention. In one embodiment, the vehicle 105 is equipped with a GPS receiver the output of which is integrated with the on-board X-ray scanning system to provide the absolute location at which each scan line is conducted. Again, output from a scanning laser is reconstructed into a 2D image to provide a quantitative analysis of the scene around the vehicle. This 2D image is archived for subsequent analysis and review.

The 2D laser scanner image may also be used to determine when the overall scan of a particular object should start and when the scan for that object is complete.

Also, optical wavelength colour CCTV images are collected at the front and sides of the vehicle, ideally using pan-tilt-zoom capability, to allow clear review of all locations around the vehicle. In one embodiment, images from the CCTV cameras are analysed to read license plate and container codes and this data is also archived along with the X-ray, GPS and all other surveillance data. Similarly, infrared cameras can also be used to monitor the scene around the vehicle to look for unexpectedly warm or cold personnel as indication of stress or presence of improvised explosive devices. This data is also archived along with X-ray and all other surveillance data.

In one embodiment, audio microphones are also installed around the vehicle to listen for sounds that are being produced in the vicinity of the vehicle. Specialist microphones with pan-tilt capability are installed to listen to sounds from specific points at some distance from the vehicle, this direction being analysed from the CCTV and IR image data.

Directional RF (Radio Frequency) antennas are installed in the skin of the vehicle to listen for the presence of electronic devices in the vicinity of the vehicle. This data is integrated with the rest of the surveillance data. Similarly, wide band antennas are installed with receiving devices that monitor communications channels that may be used by law enforcement, military and emergency services. Again, RF antennas are installed to monitor mobile phone communications including text messaging from the local region around the vehicle.

In one embodiment, chemical sensors are also installed to monitor composition of the air around the vehicle to detect trace quantities of explosives, narcotics and other relevant compounds with this data being integrated with that generated by the imaging and other sensors.

In accordance with another aspect of the present invention, an automated detection processor integrates and analyses all surveillance information from the plurality of sensors 110, in real-time, to highlight threat items for review by an operator seated inside the vehicle 105 and/or remotely through a secured wireless network. In one embodiment, data from the individual sensors is analysed for key signatures. For example, the X-ray data is analysed for detection of improvised explosive devices or for the presence of organic materials in unexpected places (such as the tyres of a car). CCTV data is analysed for license plates with cross-checking against a law enforcement database. Audio information is analysed for key words such as "bomb" or "drugs", for unexpectedly fast or deliberate phrasing which may indicate stress, or for a non-native language in the presence of a native language background for example. Once a piece of information has been analysed to comprise a threat or risk, this is escalated up a decision tree and is then compared against automated risk analysis from other sensors. If correlated risks are detected, a significant threat alarm is raised for immediate action by a human operator. If no correlated risk is detected, a moderate threat alarm is raised for review by the operator. The result is a managed flow of information where all sensor surveillance information is analysed at all times, and only significant threat information is passed up the decision tree to reach the final level of an alert to a system operator. The detection processor, in one embodiment, is a microprocessor computer running relevant code programmed for managing information and decision flow based on correlation and aggregation of the plurality of surveillance information.

Figure 23:
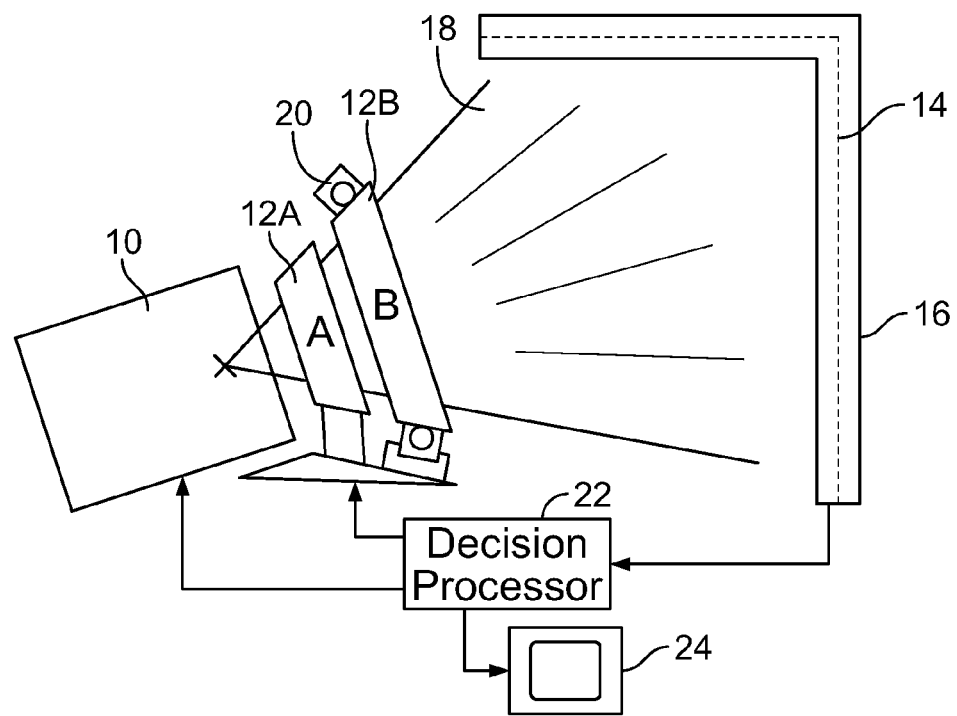
FIG. 23 is a schematic representation of a radiation imaging system that may be employed in accordance with the present invention.

Great Britain Provisional Patent Application Number 1001736.6, entitled "Image Driven Optimization", and filed on Feb. 3, 2010, and Patent Cooperation Treaty (PCT) Application Number GB2011/050182 entitled "Scanning Systems", and filed on Feb. 3, 2011 by the Applicant of the present specification, both herein incorporated by reference in their entirety disclose a scanner system comprising a radiation generator arranged to generate radiation to irradiate an object, and detection means arranged to detect the radiation after it has interacted with the object and generate a sequence of detector data sets. Referring to FIG. 23, a scanner system comprises an X-ray beam generation system which includes a shielded radiation source 10, a primary collimator set 12A and a secondary collimator set 12B, and a set of radiation detectors 14 configured into a folded L-shaped array 16, are disclosed.

The primary collimator set 12A acts to constrain the radiation emitted by the source 10 into a substantially fan-shaped beam 18. The beam 18 will typically have a fan angle in the range +/−20 degrees to +/−45 degrees with a width at the detector elements 14 in the range 0.5 mm to 50 mm. The second collimator set 12B is adjustably mounted and the position of the two second collimators 12B can be adjusted by means of actuators 20, under the control of a decision processor 22. The detectors 14 output detector signals indicative of the radiation intensity they detect and these form, after conversion and processing described in more detail below, basic image data that is input to the decision processor 22. The decision processor 22 is arranged to analyse the image data and to control the actuators 20 to control the position of the second collimator set 12B in response to the results of that analysis. The decision processor 22 is also connected to a control input of the radiation source 10 and arranged to generate and vary a control signal it provides to the control input to control the energy and timing of X-ray pulses generated by the radiation source 10. The decision processor 22 is also connected to a display 24 on which an image of the imaged object, generated from the image data, can be displayed.

By way of example, the radiation source 10 may comprise a high energy linear accelerator with a suitable target material (such as tungsten) which produces a broad X-ray spectrum with a typical beam quality in the range from 0.8 MV to 15 MV from a relatively small focal spot typically in the range 1 mm to 10 mm diameter. The radiation source 10 in this case would be pulsed with a pulse repetition frequency generally in the range 5 Hz to 1 kHz where the actual rate of pulsing is determined by the decision processor 22.

The detectors 14 in this case are advantageously fabricated from a set of scintillation crystals (generally high density scintillator such as CsI, CdW04, ZnW04, LSO, GSO and similar are preferred) which are optically coupled to a suitable light detector, such as a photodiode or photomultiplier tube. Signals from these detectors 14 converted to digital values by a suitable electronic circuit (such as a current integrator or trans impedance amplifier with bandwidth filtering followed by an analogue to digital converter) and these digital values of the sampled intensity measurements are transferred to the decision processor 22 for analysis. The primary 12A and secondary 12B collimators in this case are advantageously fabricated from high density materials such as lead and tungsten.

A plurality of active devices are installed on the vehicle 105 to help mitigate against threats that may be present proximate to the covert inspection vehicle itself. For example, a jamming device can be installed to block mobile phone communication. This device may be turned on automatically in certain situations based on results from the automated decision processor. For example, should an improvised explosive device be detected in the vicinity of the vehicle the jamming device is turned on automatically to block spoken commands to a subversive or to prevent direct communication to the trigger of the explosive device. A jamming device can also be installed to block satellite communications required in order to prevent satellite phone communications that may result in subversive activity.

In one embodiment the covert inspection vehicle 105 is operated by a single person with the primary responsibility for driving the vehicle. Surveillance data can be broadcast back to a central intelligence location in real time, as required, with download of the full archived surveillance data once the vehicle returns to its home location. The automated decision processor can action or trigger appropriate events, depending upon the decision steps programmed therein, without operator intervention to avoid the driver loosing focus on their primary task. In another embodiment, the covert inspection vehicle 105 is also provided with space for another security operative whose task is to monitor the surveillance data stream as it arrives from the plurality of sensors either in parallel with the automated decision processor or as a consequence of information from the automated decision processor. This operator is provided with two way secure wireless communication back to a central intelligence location in order to transact instructions and actions as required.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A system for detecting concealed threats in an object by simultaneously performing active and passive radiation detection, the system comprising:
   an X-ray source with a modulating device to produce a pencil beam of radiation for scanning the object, said modulating device configured to block the pencil beam at regular intervals;
   a distance sensor adapted to emit a beam of light and adapted to determine a plurality of times for said light to scatter off a plurality of surfaces of said object and return to said sensor, wherein said plurality of times are indicative of a plurality of distances from said distance sensor to said plurality of surfaces;
   a detector module for generating signals indicative of radiation backscattered by the object when the object is scanned with the pencil beam of radiation and for generating signals indicative of passive radiation that is emitted from threats within said object when the pencil beam of radiation is blocked, wherein said detector module comprises at least one detector; and
   a controller configured to cause said system to measure backscattered radiation only when the x-ray pencil beam is on, and to measure only passive radiation when the x-ray pencil beam is blocked, wherein said controller further uses the plurality of distances to implement an adaptive region based averaging method such that a size of each region is a function of a distance to the X-ray source thereby resulting in signals from regions far from the X-ray source being averaged over a larger region.

2. The system of claim 1 wherein the detector module comprises a detector array, wherein said detector array is capable of detecting both backscattered x-rays and passive radiation.

3. The system of claim 1 wherein the passive radiation detector is at least one of a gamma ray detector, a neutron detector, or a gamma-neutron detector.

4. The system of claim 3 wherein said neutron detector is used to passively measure neutrons simultaneously with backscatter radiation and passive gamma rays.

5. The system of claim 1 wherein the modulating device comprises a disc with at least one pinhole.

6. The system of claim 1 wherein the modulating device comprises a cylindrical chopper with at least one helical slit.

7. The system of claim 1 wherein the modulating device is rotated to produce a pencil beam that is blocked at regular intervals and wherein said system does not illuminate the object with radiation when the pencil beam is blocked.

8. A system for detecting concealed threats in an object by simultaneously performing active and passive radiation detection, the system comprising:
   an X-ray source with a modulating device to produce a pencil beam of radiation for scanning the object;
   a distance sensor adapted to generate a plurality of distances from said distance sensor to portions of said object;
   a detector module comprising an X-ray detector for detecting radiation backscattered by the object when scanned with the pencil beam and generating backscatter signals indicative thereof;
   a passive radiation detector for detecting radiation emitted from threats inside said object when the pencil beam is switched off and generating passive radiation threat signals indicative thereof; and
   a controller for switching the X-ray source on and off at regular intervals and, wherein said controller further uses the plurality of distances to implement an adaptive region based averaging method such that a size of each region is a function of a distance to the X-ray source thereby resulting in signals from regions further from the X-ray source being averaged over a larger region.

9. The system of claim 8 further comprising control electronics to measure backscattered radiation only when the beam is on, and to measure only passive radiation when the x-ray pencil beam is off.

10. The system of claim 8 wherein the detector module comprises a detector capable of detecting both backscattered x-rays and passive radiation.

11. The system of claim 8 wherein the passive radiation detector is at least one of a gamma ray detector, a neutron detector, or a gamma-neutron detector.

12. The system of claim 8 wherein the controller is further adapted to use the plurality of distances to geometrically correct an image of the object.

13. A method for detecting concealed threats in an object by simultaneously performing active and passive radiation detection, the method comprising:
   modulating an X-ray source to produce a pencil beam of radiation for scanning the object, such that the pencil beam is blocked at regular intervals;
   measuring distances to a plurality of surfaces of said object;
   detecting radiation backscattered by the object when scanned with the pencil beam;
   detecting passive radiation emitted from threats inside said object when the pencil beam is blocked; and
   using a filter to implement an adaptive region based averaging method using said distances such that a size of each region is a function of a distance to the X-ray source thereby resulting in signals from regions far from the X-ray source being averaged over a larger region.

14. The method of claim 13 wherein radiation is detected by using a dual-purpose detector adapted to detect both backscattered x-rays and passive radiation.

15. The method of claim 13 wherein the passive radiation is detected using a separate passive radiation detector that is at least one of a gamma ray detector, a neutron detector, or a combined gamma-neutron detector.

16. The method of claim 13 wherein said neutron detector passively measures neutrons simultaneously with backscatter radiation and passive gamma rays.

17. The method of claim 13 wherein only backscattered radiation is measured when the x-ray pencil beam is on, and only passive radiation is measured when the beam is blocked.

18. The method of claim 13 wherein the beam is modulated using a modulating device that comprises a disc with at least one pinhole.

19. The method of claim 13 wherein the beam is modulated using a modulating device that comprises a cylindrical chopper with helical slits.

20. The method of claim 13 wherein the modulating device is rotated to produce a pencil beam and is adapted to block said pencil beam at regular intervals.

* * * * *